US012059131B2

(12) United States Patent
Liu et al.

(10) Patent No.: US 12,059,131 B2
(45) Date of Patent: Aug. 13, 2024

(54) ROBOTIC DEVICE

(71) Applicant: King's College London, London (GB)

(72) Inventors: Hongbin Liu, London (GB); Julius Esmann Bernth, London (GB); Bu'Hussain Hayee, London (GB)

(73) Assignee: King's College London, London (GB)

( * ) Notice: Subject to any disclaimer, the term of this patent is extended or adjusted under 35 U.S.C. 154(b) by 719 days.

(21) Appl. No.: 16/488,392

(22) PCT Filed: Feb. 26, 2018

(86) PCT No.: PCT/GB2018/050489
§ 371 (c)(1),
(2) Date: Aug. 23, 2019

(87) PCT Pub. No.: WO2018/154326
PCT Pub. Date: Aug. 30, 2018

(65) Prior Publication Data
US 2020/0237198 A1    Jul. 30, 2020

(30) Foreign Application Priority Data

Feb. 24, 2017 (GB) ..................................... 1703056

(51) Int. Cl.
*A61B 1/00* (2006.01)
*A61B 1/005* (2006.01)
(Continued)

(52) U.S. Cl.
CPC ...... *A61B 1/00156* (2013.01); *A61B 1/00082* (2013.01); *A61B 1/0055* (2013.01);
(Continued)

(58) Field of Classification Search
CPC ............ A61B 1/00156; A61B 1/00082; A61B 1/0055; A61B 134/30; A61B 2034/301
See application file for complete search history.

(56) References Cited

U.S. PATENT DOCUMENTS

| 4,176,662 A | 12/1979 | Frazer |
| 4,389,208 A | 6/1983 | LeVeen et al. |

(Continued)

FOREIGN PATENT DOCUMENTS

| CN | 101583396 A | 11/2009 |
| DE | 102006059537 B3 | 12/2007 |

(Continued)

OTHER PUBLICATIONS

May 30, 2018, International Search Report and Written Opinion, PCT/GB2018/050489.

(Continued)

*Primary Examiner* — Anh Tuan T Nguyen
*Assistant Examiner* — Rynae E Boler
(74) *Attorney, Agent, or Firm* — Banner & Witcoff, Ltd.

(57) ABSTRACT

The present invention provides a robotic locomotive device (1) that is capable of driving itself forwards and backwards, anchoring and steering itself whilst inside a tubular structure (200), for example, the human colon, or any structure comprising two opposing walls (202, 204). In this respect, the device is made up of two or three segments (102, 104, 106) covered in an elastic material and driven by an internal actuating mechanism. All of the segments (102, 104, 106) have a concertina configuration that enable a shortening and lengthening motion. As well as contracting and extending in length, at least one of the end segments (102, 106) is capable of bending at an angle away from the longitudinal axis such that it becomes wedged or jammed between the walls (202, 204) of the tubular structure (200). That is, the end segments (102, 106) are capable of both a bending action and a contracting and extending action. The device (1) moves by alternately jamming a segment (102, 104, 106) between the walls (202, 204) of the tubular structure (200), and then contracting or extending the segments (102, 104, 106) to inch the device (1) forward with a more effective locomotive action. As such, the present invention provides a simplified design that is more robust to harsh or unclean environments, whilst still maintaining the level of performance required from such a device.

5 Claims, 23 Drawing Sheets

(51) Int. Cl.
*A61B 34/30* (2016.01)
*A61B 1/31* (2006.01)
*A61B 10/04* (2006.01)
*A61M 25/01* (2006.01)
*A61M 25/10* (2013.01)

(52) U.S. Cl.
CPC .............. *A61B 34/30* (2016.02); *A61B 1/31* (2013.01); *A61B 10/04* (2013.01); *A61B 2034/301* (2016.02); *A61M 25/0116* (2013.01); *A61M 25/1018* (2013.01); *A61M 2025/1084* (2013.01); *A61M 2025/1086* (2013.01)

(56) References Cited

U.S. PATENT DOCUMENTS

| | | | | |
|---|---|---|---|---|
| 5,662,587 | A * | 9/1997 | Grundfest | A61B 34/30 600/116 |
| 6,402,686 | B1 | 6/2002 | Ouchi | |
| 2003/0065250 | A1 | 4/2003 | Chiel et al. | |
| 2003/0149338 | A1 * | 8/2003 | Francois | F15B 15/103 600/152 |
| 2004/0073082 | A1 | 4/2004 | Phee Soo Jay et al. | |
| 2010/0249505 | A1 * | 9/2010 | Shoham | A61M 25/0122 600/115 |
| 2012/0035440 | A1 | 2/2012 | Ferren et al. | |
| 2015/0367101 | A1 | 12/2015 | Shoham et al. | |
| 2017/0143192 | A1 * | 5/2017 | Nagase | A61B 1/00148 |
| 2017/0157363 | A1 * | 6/2017 | Barrish | A61M 25/0136 |

FOREIGN PATENT DOCUMENTS

| | | |
|---|---|---|
| JP | H01-280716 A | 11/1989 |
| JP | 2009018116 A | 1/2009 |
| JP | 2009066167 A | 4/2009 |
| JP | 2009520507 A | 5/2009 |

OTHER PUBLICATIONS

Jul. 25, 2017, Search Report, GB1703056.0.

CN Office Action dated Apr. 6, 2021—Application No. 201880013747.7.

Notice of Reasons for Refusal Japanese Patent Application No. 2019546344.

* cited by examiner (a)
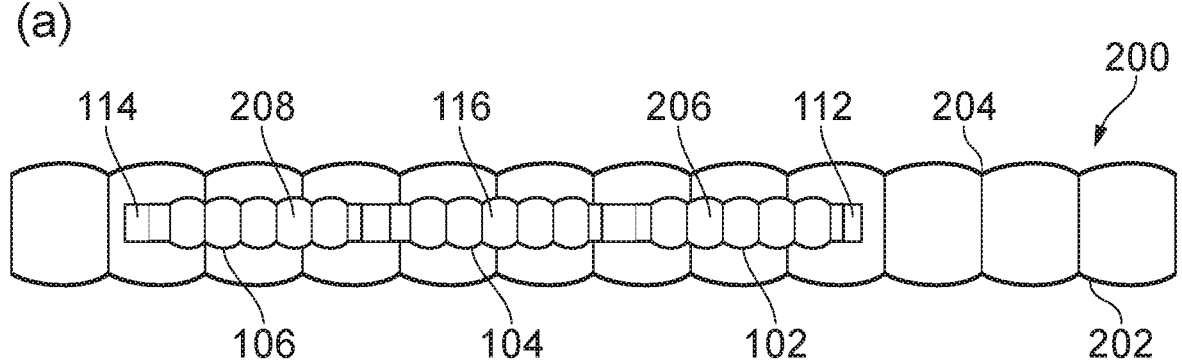
(b)
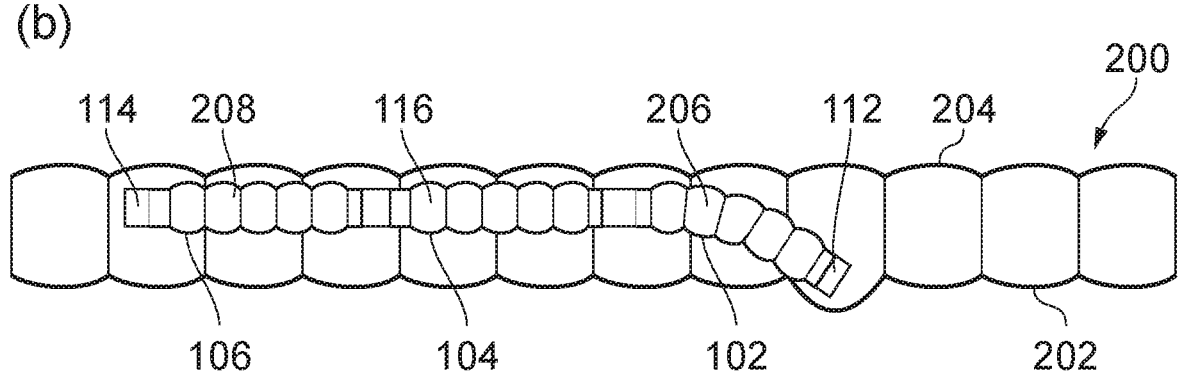
(c)
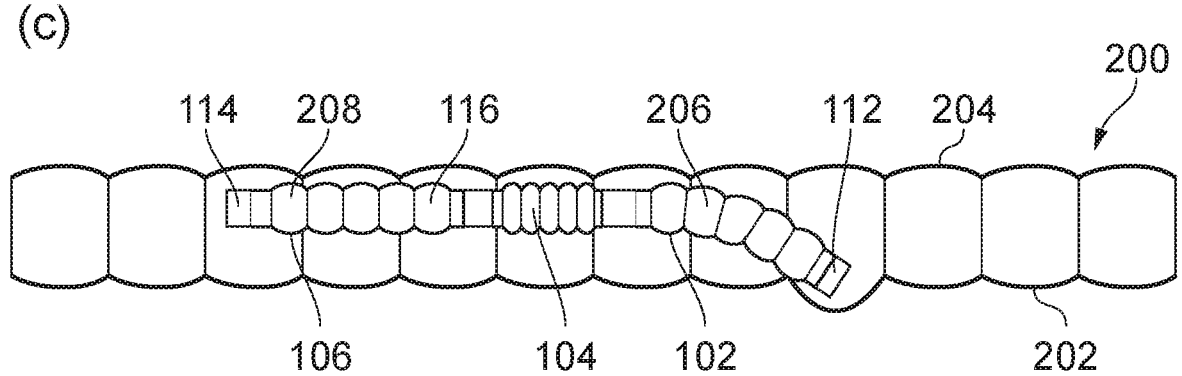
FIG. 3

(d)
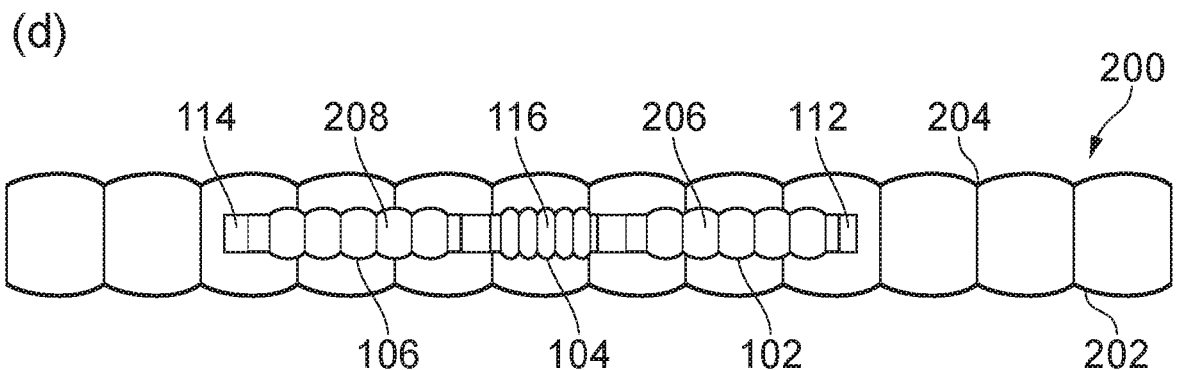
(e)
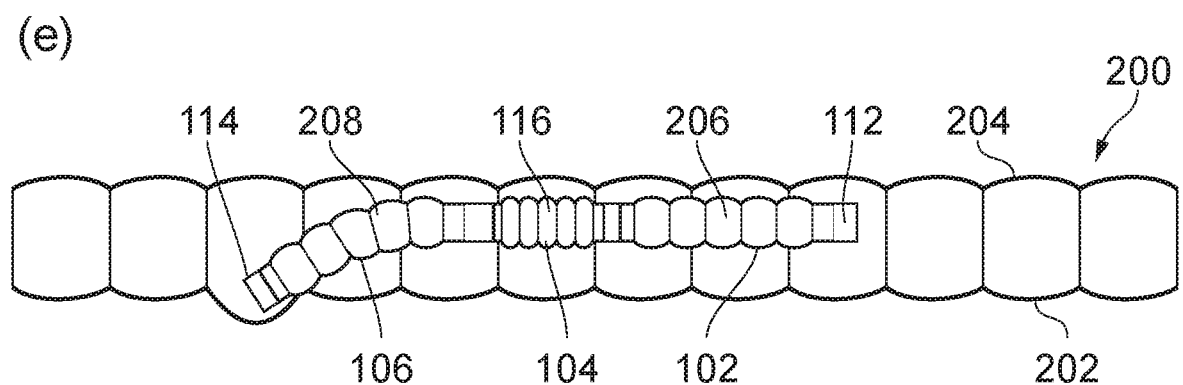
(f)
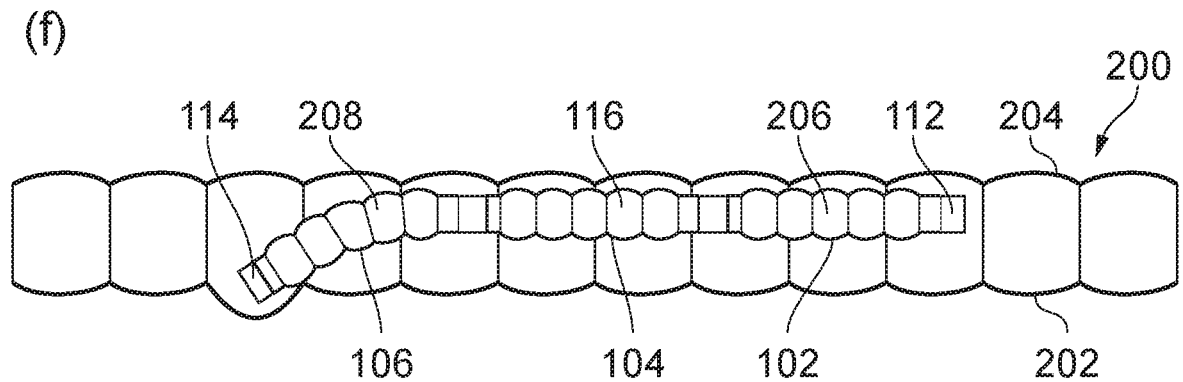
FIG. 3 (Continued)

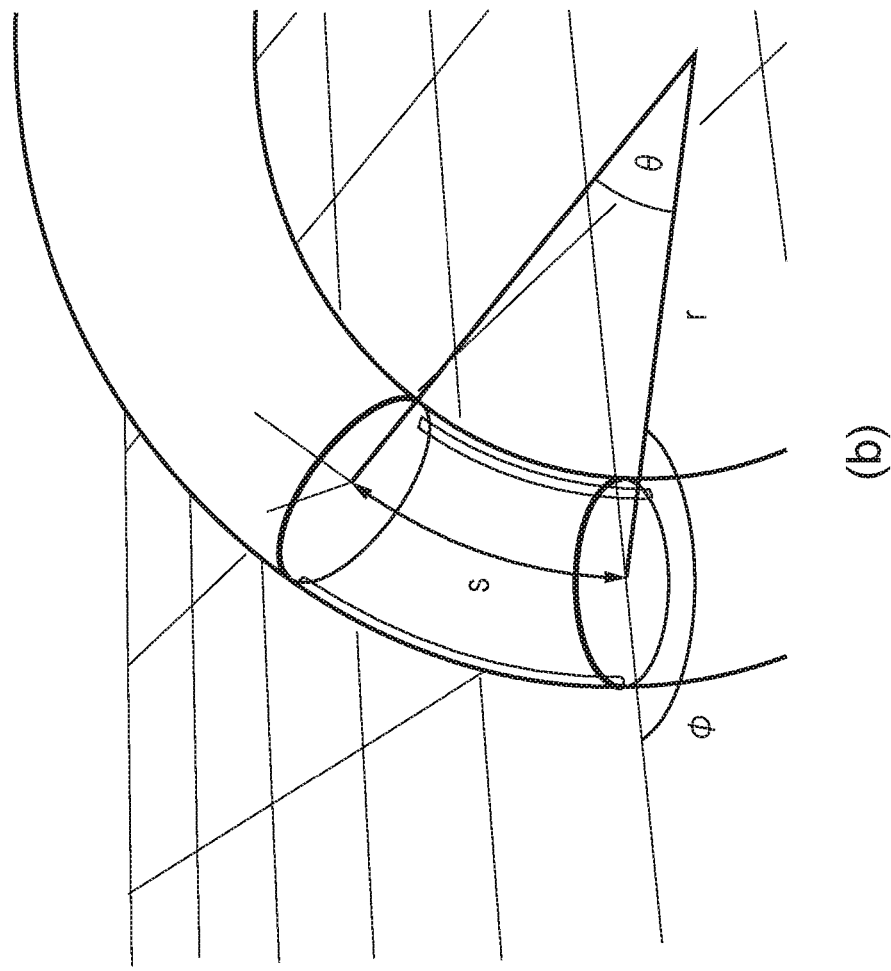
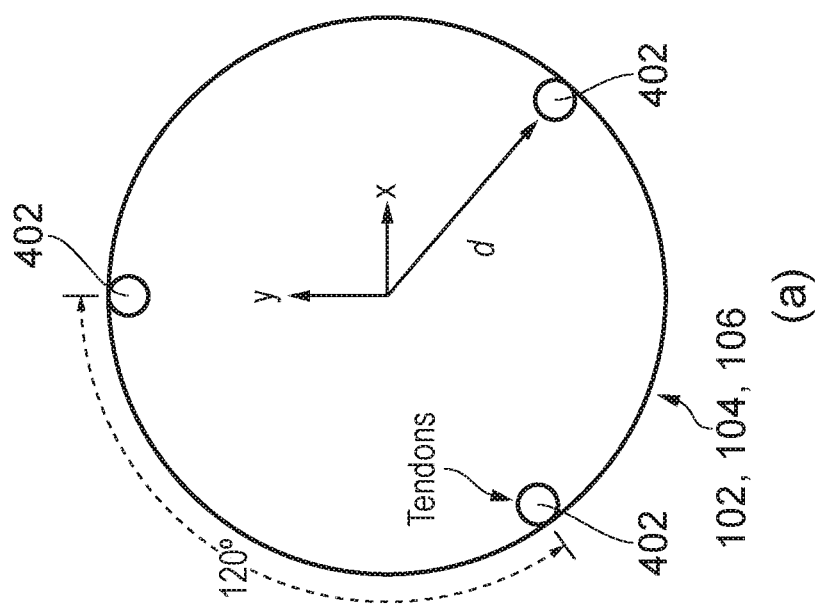
FIG. 17

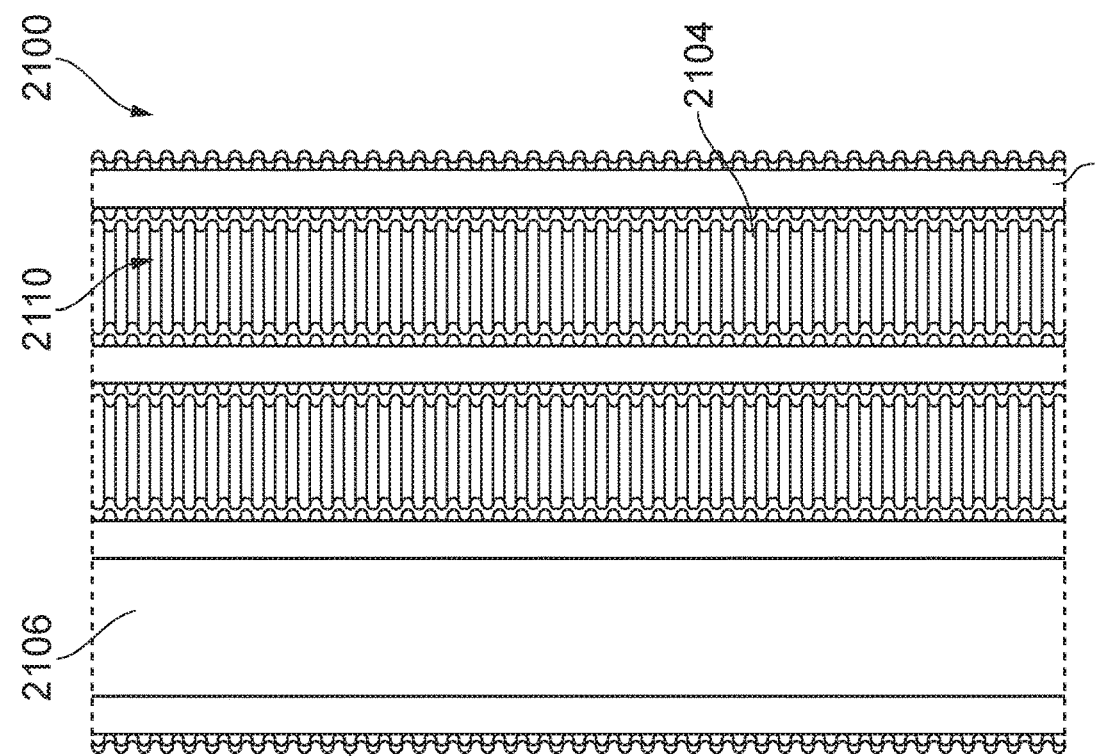
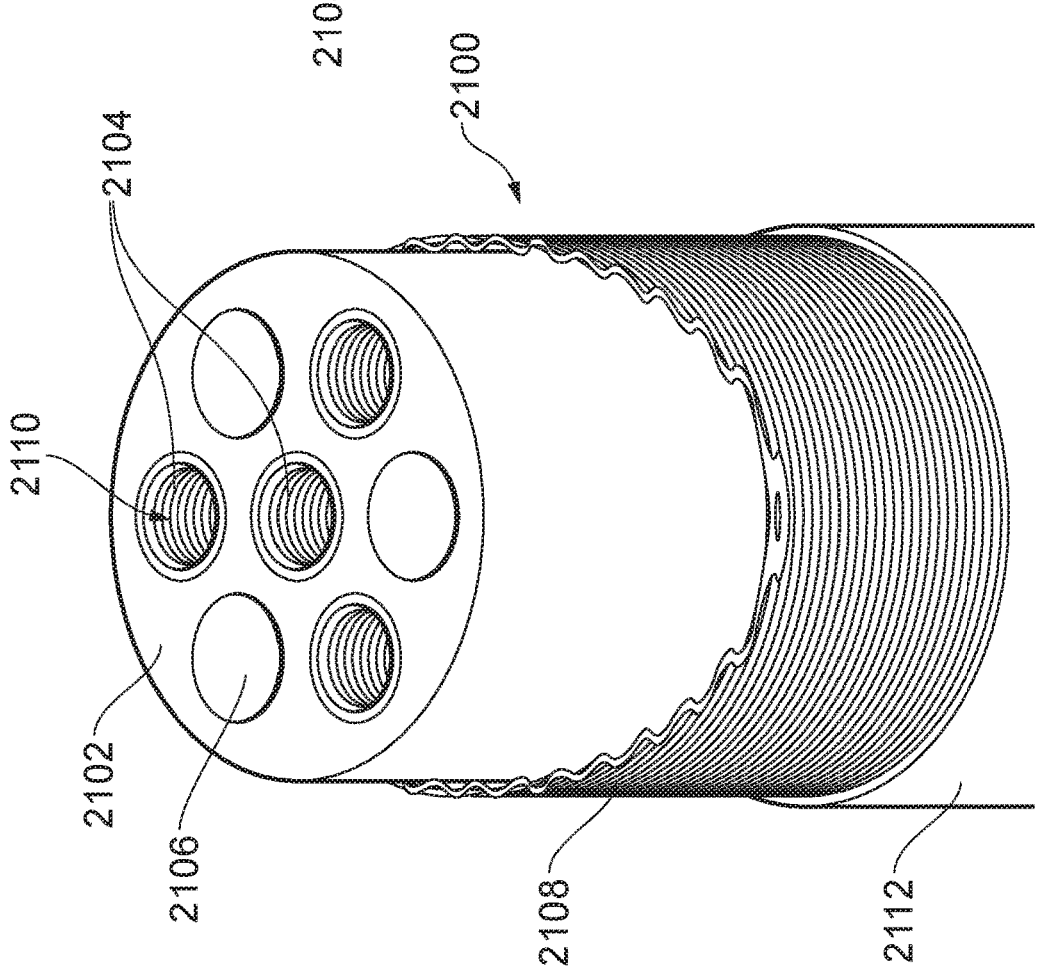

ROBOTIC DEVICE

CROSS-REFERENCE TO RELATED APPLICATIONS

This application is a U.S. National Stage application under 35 U.S.C. § 371 of International Application PCT/GB2018/050489 (published as WO 2018/154326 A1), filed Feb. 26, 2018, which claims the benefit of priority to Application GB 1703056.0, filed Feb. 24, 2017. Benefit of the filing date of each of these prior applications is hereby claimed. Each of these prior applications is hereby incorporated by reference in their entirety.

TECHNICAL FIELD

The present invention relates to a self-steering robotic locomotive device with adaptive anchoring. In particular, the present invention relates to a multi-segment locomotive device with segment bending anchoring for use in the exploration of small tubular structures, particularly those that are in hard to reach locations, of considerable length, highly torturous and/or compliant, and in which existing technology struggles to effectively manoeuvre.

BACKGROUND TO THE INVENTION AND PRIOR ART

There are many structures, natural or man-made, that contain smaller tubular structures. An example of such a structure occurring in nature is the human body, which has tubular structures such as the intestine and oesophagus. An example of a man made structure may be a building having a network of plumbing pipework. It is often necessary to survey the inside of the tubular structures whilst in situ. However, where the tubular structures are very long and/or torturous and therefore difficult to reach, or in cases such as the human body where it is necessary to be as minimally invasive as possible, a device is required that can easily manoeuvre along the inside of the tubular structure whilst being controlled externally.

An example of such a device is an endoscope, such as that shown in FIG. 1, commonly used to screen for colon cancer or stomach cancer. Endoscopes can also be used for performing biopsies to test suspect tissue or removing tumours or polyps all together. Typical endoscopes are long, slender, flexible instruments with a camera and light at the distal end, with working channels to introduce flexible instruments[1]. To move through the human colon, the device is manually pushed by the endoscopist. The distal end of the device can be steered, allowing some control of the direction of movement. The rest of the body is passively flexible. When the endoscopist pushes the end of the endoscope to make the scope progress, the passively flexible part of the endoscope can cause the colon to deform significantly. As a result, procedures such as colonoscopy can be extremely uncomfortable for patients. There is evidence[2] that the fear of this discomfort is one of the main reasons that patients avoid regular screenings and thus a significant contributing factor to the number of cases of colorectal cancer.

Although these endoscopes' flexibility is what enables them to be pushed, their flexibility being that which enables them to easily travel inside the human body, this very same flexibility can be the source of various difficulties. For example, when a flexible endoscope is advanced through an intestine, the endoscopist pushes from one end. The portion of the flexible shaft inside the colon then exerts a force on the intestinal wall. Additionally, as the body of the endoscope is so flexible, it is also possible that the resistance inside the colon prevents the distal end from advancing when pushed. As a result, part of the flexible shaft may loop back on itself, again causing large deformations of the intestine. Both situations cause significant discomfort for patients.[3]

Double-balloon enteroscopy (push-and-pull enteroscopy) is a new method that allows complete visualization, biopsy, and treatment in the small bower. Double-balloon enteroscopes use two balloons to progress through the intestine; one at the end of an over-tube and another attached to the end of the endoscopes. By using the friction of the interface of two balloons and the intestinal wall, the enteroscope can be inserted further into the small intestine without forming unnecessary loops.

Capsule endoscopy involves a patient swallowing a small, pill-shaped device with a camera mounted inside of it. This then passively moves through the entire digestive tract, as food would, capturing images along the way and transmitting them to an external view-screen[6, 7]. The issue with such devices is that it cannot be controlled and therefore produces hours of footage which must be examined thoroughly to make a diagnosis. In the event that a suspicious area was found, there is also no option to reposition the camera for a more detailed inspection.

Several researchers have been developing potential robotic solutions to replace traditional endoscopes. For such a device, locomotion is an essential factor. The robot must be able to propel itself through the colon, carrying a miniature camera, biopsy and water channel necessary for the procedure. Additionally, a steerable distal end is also needed to control the viewing angle of the camera and to actively guide the biopsy tool. Furthermore, if the process of moving through the colon is automated, the doctor is able to fully concentrate on making a diagnosis according to the images captured by the device[8].

Many locomotion techniques for robotic endoscopes are based on the movements of worm-like creatures. For example, U.S. Pat. No. 4,176,662 relates to a device for robotic colonoscopy which adopted the crawling method used by inchworms. In 1995, an endoscope system based on the MEDI-WORM was designed, which used compressed gas as a power source and rubber balloon as a driver to simulate the peristaltic movement of an earthworm[9]. In 1996, a self-propelling robotic endoscope was developed that was able to move semi-autonomously in the colon but could only move forward and not backward[10]. Later in 1999, a vision-guided micro-robotic colonoscopy system was created. The system was a vision-guided autonomous system which was able to move, test, analyse and diagnose in the human colon. The study included the establishment of the mathematical model of steering the micro-robot, and theoretical study on path planning based on sensor data[11]. Other designs rely on geared DC motors to actuate linkages between segments, thus producing peristaltic motion[12], and include an anchoring mechanism which allows either the front-most or rear-most segment to increase friction on its surrounding environment[13].

Many worm-inspired designs have introduced a soft mesh body. An early mesh-based robot consisted of three pneumatically actuated segments specifically intended for use in colonoscopy[14], in which bladder structures based on artificial muscles were inflated to cause an expansion and contraction in a particular segment. Doing this in proper sequence, peristaltic motion was achieved. Other devices rely on shape memory alloy (SMA) actuators to produce a worm-like crawling motion[15, 16]. To ensure such a device move forwards, small hooks are embedded on the outer skin of the robot to increase friction in one direction. While effective during forward movement, this feature does, however, prevent the device from moving backwards.

Further designs consist of a spring-like, soft mesh which is then deformed by a series of SMA actuators[17]. The arrangement of the actuators is inspired by how circular and longitudinal muscle fibres function in common earth worms. Motion is then achieved through peristalsis.

In addition to worm-inspired devices, some robotic endoscopes take inspiration from the serpentine locomotion of a snake, where the body forms a series of S-shaped horizontal loops and each loop pushes against any surface resistance to move forward[18].

A further example of robotic devices for endoscopic procedures already known in the art is provided by U.S. Pat. No. 5,662,587. The device described in this document comprises a plurality of segments that are attached to each other.

Traction segments embrace the lumen walls, whilst other segments include actuators that cause the endoscope to locally deform its shape via bending, extending, or some combination of bending and extension. A method is provided to sequence the action of the segments to cause inchworm-like or snake-like locomotion, or a combination of them through a curved and flexible lumen.

SUMMARY OF THE INVENTION

Embodiments of the present invention address the above noted problems by providing a robotic locomotive device that is capable of driving itself forwards and backwards, anchoring and steering itself whilst inside a tubular structure, for example, the human colon, or any structure comprising two opposing walls. In this respect, the device is made up of two or three segments covered in an elastic material and driven by an internal actuating mechanism. All of the segments have a concertina configuration that enable a shortening and lengthening motion. As well as contracting and extending in length, at least one of the end segments is capable of bending at an angle away from the longitudinal axis such that it becomes wedged or jammed between the walls of the tubular structure. That is, the end segments are capable of both a bending action and a contracting and extending action. The device moves by alternately jamming or anchoring a segment between the walls of the tubular structure, and then contracting or extending the segments to inch the device forward with a more effective locomotive action. The segment may also bend so as to hook around a corner or protrusion of the environment. In the case of a compliant environment, the segment may bend so as to form a fold in the walls of the structure and proceed to pinch it. As such, the present invention provides a simplified design that is more robust to harsh or unclean environments, whilst still maintaining the level of performance required from such a device.

The angle at which a segment is bent can be adjusted according to the size of the tubular structure. That is, the segment will be bent at an angle that is sufficient to ensure that the bending will result in contact with the walls of the tubular structure, but not to the extent that it exerts an excessive force, the magnitude of which can be regulated through precise actuator control. This sequence of movements is repeated such that the device moves through the tubular structure with a locomotive action similar to that of a worm.

Furthermore, the elastic material housing is adaptive so as to allow on the fly adjustments to the properties of the device. In this respect, the mesh expands and contracts with the longitudinal movement of the segments to adjust the diameter and the stiffness of the segment. When a segment contracts longitudinally and shortens, the mesh housing expands and thereby increases the diameter and the stiffness of the segment. This helps to create a more secure anchoring point and hold the device in place, preventing the device from slipping backwards. Conversely, when the segment extends longitudinally and lengthens, the mesh contracts to its original configuration and thereby reduces the diameter and the stiffness of the segment. When the device is moving forwards, this helps the device to move smoothly through the tubular structure.

In one aspect, the present invention provide a locomotive robotic device for use inside a structure having opposing walls, the device having an elongate body comprising a first segment, and a second segment contiguous to the first segment, wherein the first and second segments are configured to contract and extend along the longitudinal axis of the elongate body, and wherein the first segment is further configured to bend at angle to the longitudinal axis of the elongate body such that, upon bending, the first segment becomes wedged between a first wall and a second wall of the structure.

As such, the segment used to anchor the device within the structure is capable of bending to provide the anchoring, as well as contracting and extending to help drive the device forwards within the structure. Therefore, both segments are able to contribute to the forwards movement.

The first segment may be further configured to bend to the extent that the first segment pinches a wall of the structure. This helps to further anchor the device within the structure. The first segment may also be configured to bend to the extent that the first segment hooks a corner of the wall of the structure.

The angle at which the first segment bends may be dependent on the diameter of the structure. As such, the angle at which the first segment bends may be controlled such that it is sufficient to anchor the first segment between the walls of the structure, but not to the extent that the first segment exerts an excessive amount of force on the walls of the structure. This is important for preventing damage to the structure. In this respect, the amount of force exerted on the walls can be controlled by the means used to actuate the first segment.

The device may further comprise a third segment contiguous to the second segment, wherein the third segment is configured to contract and extend along the longitudinal axis of the elongate body, and bend at angle to the longitudinal axis of the elongate body such that, upon bending, the third segment becomes wedged between the first and second walls of the structure.

Adding this third segment to the device provides an additional step to the locomotive sequence, thereby increasing the speed and efficacy of the device. For example, the third segment is able to contract linearly before it anchors itself between the walls of the structure by bending, and then extends linearly with the second segment to drive the first segment forward. Moreover, by including a third segment that is capable of a contracting and extending action, as well as a bending action, the device is capable of moving in both directions along the structure.

The third segment may also be configured to bend to the extent that it pinches a wall of the structure. The angle at which the third segment bends may also be dependent on the diameter of the structure. The third segment may also be configured to bend to the extent that the third segment hooks a corner of the wall of the structure.

The elongate body may also comprise an outer sleeve, wherein the outer sleeve may be an elastic mesh.

The outer sleeve may comprise a surface configured in use to increase friction in a first direction along the longitudinal axis of the elongate body. That is, if the device moves in a particular direction, the outer sleeve is configured to increase friction with the walls of the tubular structure in which the device is deployed. This helps to prevent the device from slipping backwards, and further helps the device to move itself around corners.

The outer sleeve may comprise a surface configured in use to increase friction in a first direction and a second opposing direction along the longitudinal axis of the elongate body. In doing so, the outer sleeve is configured to help prevent the sleeve from slipping back in either direction.

In this respect, the surface may comprise a plurality of fish scale or cilia-like projections moveable between a first position and a second position. The first position may comprise the plurality of fish scale or cilia-like projections being substantially parallel to the longitudinal axis of the elongate body, whilst the second position comprises the plurality of fish scale or cilia-like projections being substantially perpendicular to the longitudinal axis of the elongate body. As such, when moving in one direction, the fish scale or cilia-like projections may lay flat against the surface of the device. When moving in the opposite direction, the fish scale or cilia-like projections then stand upwards so that they are perpendicular to the surface of the elongate body such that they grip against the walls of the tubular structure in which they are deployed. As such, the fish scale or cilia-like projections are configured to change orientation so as to regulate surface friction when the device changes bending angle.

The outer sleeve may be configured to change in diameter and/or stiffness in dependence on a movement of one or more parts of the elongate body. For example, when a segment contracts along the longitudinal axis, the outer sleeve may increase in diameter and stiffness. Conversely, when a segment extends along the longitudinal axis, the outer sleeve may decrease in diameter and stiffness.

The first and second segments may be hydraulically or pneumatically actuated.

In this respect, the first and second segments may comprise a flexible body having one or more actuation chambers extending therethrough, wherein the one or more actuation chambers are configured to receive a fluid. As such, fluid is pumped in and out of the actuation chambers causing them to extend and contract along the longitudinal axis of the elongate body, and/or bend at an angle to the longitudinal axis of the elongate body.

The flexible body may further comprise at least one cavity extending therethrough, the at least one cavity comprising an internal reinforcement means.

Preferably, the flexible body comprises two or more cavities.

The internal reinforcement means may be configured to constrain lateral expansion of the one or more actuation chambers as fluid is received thereto. By constraining lateral expansion of the actuation chambers, the actuation chambers are caused to extend and contract longitudinally instead as fluid is pumped in and out of the actuation chambers. Furthermore, the constraint on the lateral expansion provided by the internal reinforcement means reduces cross-coupling between the actuation chambers by preventing the actuation chambers from interfering with one another. Consequently, these internal reinforcement means also prevent the cavity from collapsing inwards when adjacent actuating chambers are actuated. This is also important for protecting other instruments and devices that may be enclosed within the cavity.

The internal reinforcement means may be configured to contract, extend and/or bend with the flexible body. That is, whilst sufficiently stiff so as to prevent the actuation chambers from laterally expanding, the internal reinforcement means are configured such that they are capable of extending and contracting along the longitudinal axis of the device, as well as bending at an angle to the longitudinal axis.

The radial stiffness of the internal reinforcement means may be such that radial expansion of the one or more actuation chambers is constrained. That is to say, the internal reinforcement means has a structure that is suitable for preventing any radially outwards expansion by the actuation chambers.

The internal reinforcement means may one of: a spring, a coil, a wound thread of resilient material, a concertina-like support structure, a bellows structure, or a series of resilient hoops.

The at least one cavity may be configured to receive one or more of: a medical instrument, an imaging device, and a fluid.

The flexible body may be enclosed in an external reinforcement means, wherein the external reinforcement means may be configured to constrain lateral expansion of the one or more actuation chambers as fluid is received thereto. As noted above, by constraining lateral expansion of the actuation chambers, the actuation chambers are caused to extend and contract longitudinally instead as fluid is pumped in and out of the actuation chambers.

The external reinforcement means may also be configured to contract, extend and/or bend with the flexible body. That is, whilst sufficiently stiff so as to prevent the actuation chambers from laterally expanding, the external reinforcement means is configured such that it is capable of extending and contracting along the longitudinal axis of the device, as well as bending at an angle to the longitudinal axis.

The radial stiffness of the external reinforcement means may be such that radial expansion of the one or more actuation chambers is constrained.

The external reinforcement means may be one of: a spring, a coil, a wound thread of resilient material, a concertina-like support structure, a bellows structure, or a series of resilient hoops.

The flexible body may be formed of an elastomeric material. It will be appreciated that the flexible body may be formed of any suitable elastomeric material, for example, a rubber material.

The elongate body may be configured to communicate with a remote control system. In this respect, the elongate body may comprise a sensor system arranged to output information to the control system regarding the position and/or orientation of the elongate body inside the structure.

In a further aspect, the present invention provides a locomotive robotic device for use inside a structure having opposing walls, the device having an elongate body comprising a plurality of segments configured to move in at least a first direction, and an outer sleeve surrounding the plurality of segments, wherein the diameter and/or stiffness of the outer sleeve is arranged to change in dependence on a movement of one or more of the plurality of segments in the first direction.

As such, the outer sleeve adapts with the movement of the device in order to provide more secure anchoring and a smoother movement along the structure.

The outer sleeve may comprise an elastic material, wherein the elastic material may be an elastic mesh.

The first direction may be along the longitudinal axis of the elongate body such that the plurality of segments are arranged to increase and decrease in length.

Where the first direction is along the longitudinal axis of the elongate body, the diameter and/or stiffness of the outer sleeve may be arranged to increase in response to a decrease in length. As such, when a segment shortens in length, the outer sleeve becomes wider and stiffer. This helps to anchor the segment to the structure, and helps prevent the device from slipping backwards.

Where the first direction is along the longitudinal axis of the elongate body, the diameter and/or stiffness of the outer sleeve may be arranged to decrease in response to an increase in length. As such, when a segment lengthens back out, the outer sleeve becomes narrower and softer. This enables the device to easily conform to the curvature of the structure during forward movement, which helps the device to move smoothly along the structure. In applications such as colonoscopy, this is important for preventing patient discomfort.

In one application, the device according to any of the arrangements described above may be an endoscope.

In a further aspect, the present invention provides a system comprising a device according to any of the arrangements described above, and a control system arranged to output drive signals to the device.

In a further aspect, the present invention provides a locomotive device, the device having an elongate body comprising a plurality of segments, wherein a segment comprises a flexible body, and one or more actuation chambers extending along the length of the flexible body, wherein the one or more actuation chambers are configured to be actuated by means of a fluid to thereby cause the flexible body to contract and extend along the longitudinal axis of the device and/or bend at an angle to the longitudinal axis of the device.

As such, fluid is pumped in and out of the actuation chambers causing them to extend and contract along the longitudinal axis of the elongate body, and/or bend at an angle to the longitudinal axis of the elongate body.

The flexible body may further comprise at least one cavity extending therethrough, the at least one cavity comprising an internal reinforcement means.

Preferably, the flexible body comprises two or more cavities.

The internal reinforcement means may be configured to constrain lateral expansion of the one or more actuation chambers as fluid is received thereto. By constraining lateral expansion of the actuation chambers, the actuation chambers are caused to extend and contract longitudinally instead as fluid is pumped in and out of the actuation chambers. Furthermore, the constraint on the lateral expansion provided by the internal reinforcement means reduces cross-coupling between the actuation chambers by preventing the actuation chambers from interfering with one another.

Consequently, these internal reinforcement means also prevent the cavity from collapsing inwards when adjacent actuating chambers are actuated. This is also important for protecting other instruments and devices that may be enclosed within the cavity.

The internal reinforcement means may be configured to contract, extend and/or bend with the flexible body. That is, whilst sufficiently stiff so as to prevent the actuation chambers from laterally expanding, the internal reinforcement means are configured such that they are capable of extending and contracting along the longitudinal axis of the device, as well as bending at an angle to the longitudinal axis.

The radial stiffness of the internal reinforcement means may be such that radial expansion of the one or more actuation chambers is constrained. That is to say, the internal reinforcement means has a structure that is suitable of prevent any radially outwards expansion by the actuation chambers.

The internal reinforcement means may one of: a spring, a coil, a wound thread of resilient material, a concertina-like support structure, a bellows structure, or a series of resilient hoops.

The at least one cavity may be configured to receive one or more of: a medical instrument, an imaging device, and a fluid.

The flexible body may be enclosed in an external reinforcement means, wherein the external reinforcement means may be configured to constrain lateral expansion of the one or more actuation chambers as fluid is received thereto. As noted above, by constraining lateral expansion of the actuation chambers, the actuation chambers are caused to extend and contract longitudinally instead as fluid is pumped in and out of the actuation chambers.

The external reinforcement means may also be configured to contract, extend and/or bend with the flexible body. That is, whilst sufficiently stiff so as to prevent the actuation chambers from laterally expanding, the external reinforcement means is configured such that it is capable of extending and contracting along the longitudinal axis of the device, as well as bending at an angle to the longitudinal axis.

The radial stiffness of the external reinforcement means may be such that radial expansion of the one or more actuation chambers is constrained.

The external reinforcement means may be one of: a spring, a coil, a wound thread of resilient material, a concertina-like support structure, a bellows structure, or a series of resilient hoops.

The flexible body may be formed of an elastomeric material. It will be appreciated that the flexible body may be formed of any suitable elastomeric material, for example, a rubber material.

The device may further comprise a pump configured to pump a fluid in and out of the one or more actuation chambers.

The device may further comprise an outer sleeve encasing the plurality of segments.

The outer sleeve may comprise a surface configured in use to increase friction in a first direction along the longitudinal axis of the elongate body. That is, if the device moves in a particular direction, the outer sleeve is configured to increase friction with the walls of the tubular structure in which the device is deployed. This helps to prevent the device from slipping backwards, and further helps the device to manoeuvre around corners.

The outer sleeve may comprise a surface configured in use to increase friction in a first direction and a second opposing direction along the longitudinal axis of the device. In doing so, the outer sleeve is configured to help prevent the sleeve from slipping back in either direction.

In this respect, the surface may comprise a plurality of cilia-like projections moveable between a first position and a second position.

The first position may comprise the plurality of fish scale or cilia-like projections being substantially parallel to the longitudinal axis of the device, whilst the second position comprises the plurality of fish scale or cilia-like projections being substantially perpendicular to the longitudinal axis of the device. As such, when moving in one direction, the fish scale or cilia-like projections may lay flat against the surface of the device. When moving in the opposite direction, the fish scale or cilia-like projections then stand upwards so that they are perpendicular to the surface of the elongate body such that they grip against the walls of the tubular structure in which they are deployed. As such, the fish scale or cilia-like projections are configured to change orientation so as to regulate surface friction when a segment changes bending angle.

In one application, the device according to any of the arrangements described above may be an endoscope.

BRIEF DESCRIPTION OF THE DRAWINGS

Further features and advantages of the present invention will become apparent from the following description of embodiments thereof, presented by way of example only, and by reference to the drawings, wherein:

FIG. 3 illustrates the operation of an embodiment of the present invention;

FIGS. 17a-b illustrate shape estimation using embodiments of the present invention;

FIGS. 21a-b illustrate a device according to an embodiment of the present invention;

DETAILED DESCRIPTION OF DRAWINGS

Figure 1:
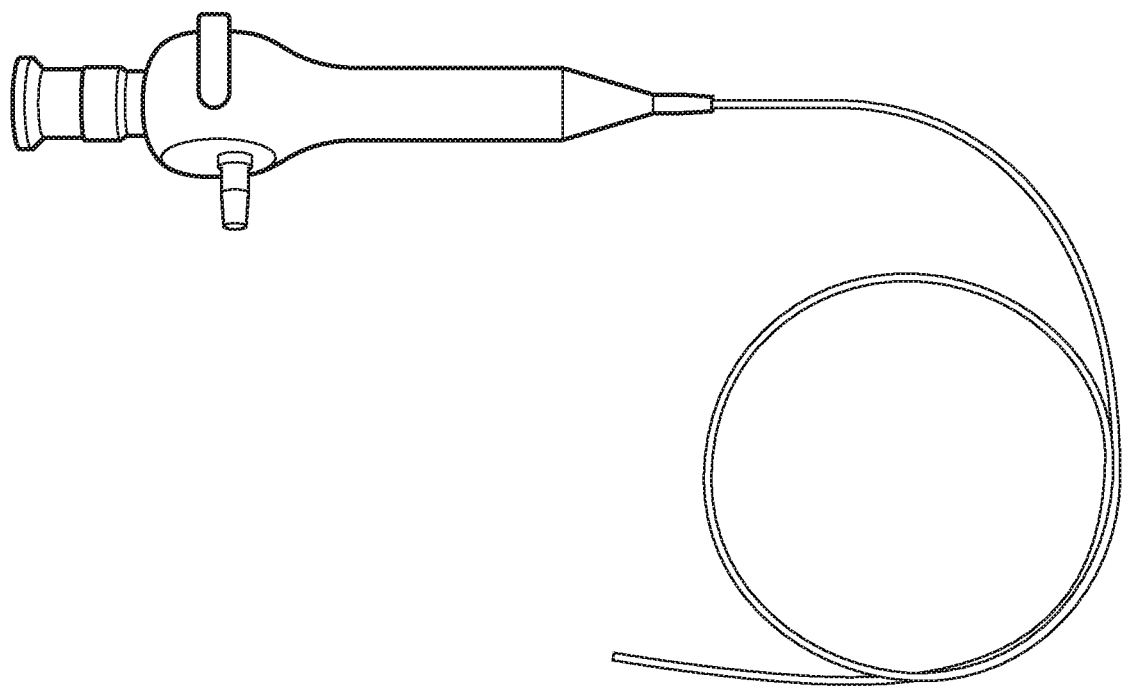
FIG. 1 illustrates a prior art endoscope.
Figure 2:
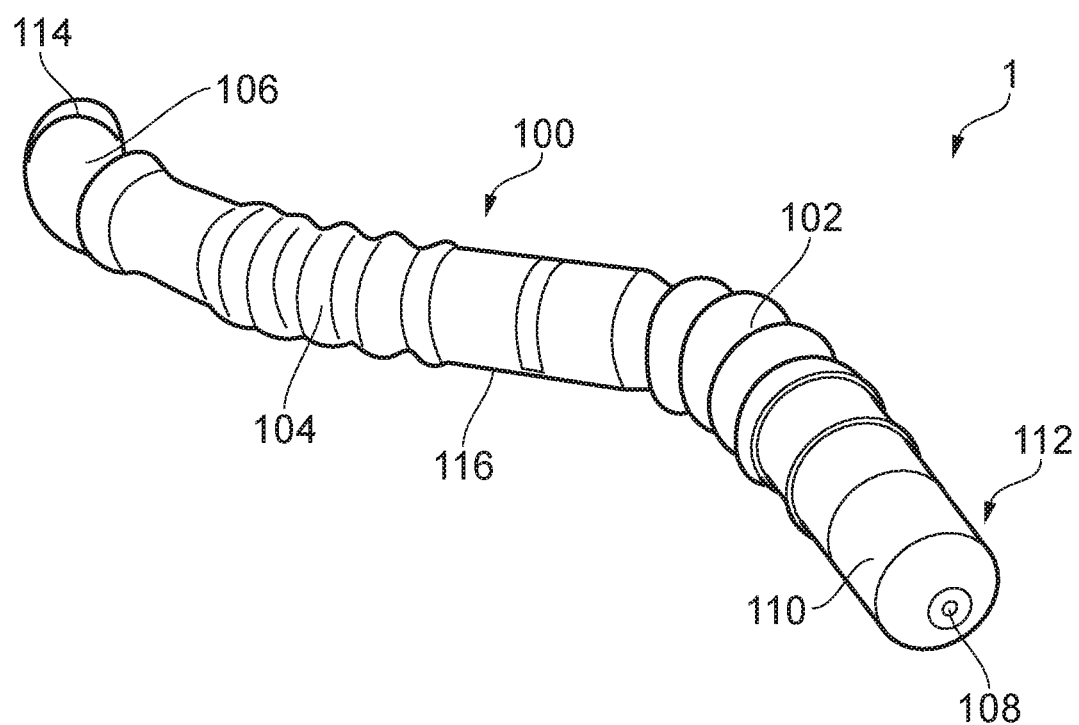
FIG. 2 illustrates a device according to an embodiment of the present invention.

FIG. 2 illustrates a robotic device 1 according to an embodiment of the present invention. The device 1 has an elongate body 100 comprising three segments; a first end segment 102, a middle segment 104 and a second end segment 106. The elongate body 100 is covered in an outer sleeve 116 that is made of a material having elastic properties. In this example, the outer sleeve 116 is an elastic mesh. In this example, the device 1 also comprises a camera 108 disposed within a housing 110 on the tip 112 of the first end segment 102. However, a camera may also be disposed at the tip 114 of the second end segment 106 and/or replaced with some other sensing equipment according to the application for which it is intended.

Each segment 102, 104, 106 consists of an actuating mechanism (not shown) for driving the movement of each segment 102, 104, 106. Each segment 102, 104, 106 has a concertina-type configuration similar to that of the bendable portion of an articulated straw. As such, each segment 102, 104, 106 has a linear degree of freedom (DOF) such that it is capable of contracting and extending along the longitudinal axis of the device 1. The middle segment 104 only has this single linear DOF, whereas the first end segment 102 and the second end segment 104 also have two rotational DOF to allow bending about two axes. As such, the end segments 102, 106 have three DOF. However, in some arrangements, the end segments 102, 106 may have only two DOF; a linear DOF and a single rotational DOF to allow bending about a single axis. In such an arrangement, a single, new DOF is added to allow the two end segments 102, 106 to rotate about their longitudinal axis relative to each other. This new DOF may be placed anywhere on the body 100 as long as it produces relative rotation between the two end segments 102, 106. Such an arrangement is capable of the same locomotive motion as a device 1 where the end segments 102, 104 have three DOF. In all of the above arrangements, the device 1 may also be capable of rotating about its longitudinal axis.

The soft mesh 116 housing the device 1 is also adaptive in that it contracts and expands with the movement of the device 1. In this respect, when a segment 102, 104, 106 contracts along the longitudinal axis, the mesh 116 covering that segment 102, 104, 106 expands outwards and thereby increases the diameter of that segment 102, 104, 106. The compression of the mesh 116 as the segment shortens in length also increases the stiffness of the segment 102, 104, 106. Conversely, when a segment 102, 104, 106 extends along the longitudinal axis, it pulls the mesh 116 back to its original configuration, and thereby decreases the diameter of the segment 102, 104, 106. Similarly, the extension of the segment 102, 104, 106 causes the mesh 116 to soften. This will be described in more detail below.

The actuating mechanism used to move the device 1 is remotely controlled by some suitable control equipment (not shown) that communicates with a feedback system provided within the device 1. As an example, the actuating mechanism may comprise tendons that are wound around pulleys which are mounted on DC motors, as described in more detail below with reference to FIGS. 4a and 4b. The motors controlling the tendons may then be controlled by some external control system, as described in more detail below with reference to FIGS. 10 and 12. To this end, the actuating mechanism is provided with a sensor system which provides feedback to the control system. The control system will then process the feedback signal received from the sensor system to generate a control signal that is output to the motors. As such, the continuous feedback loop between the actuating mechanism and the control system means that the device 1 is able to steer itself through the tubular structure in which it has been inserted.

The operation of the device 1 will now be described with reference to FIG. 3. The device 1 is first deposited within a tubular structure 200, as shown in step 3(a). At this stage, all three segments 102, 104, 106 are fully extended and lying in the same longitudinal plane such that the device 1 as a whole has a straight configuration. To start moving along the tubular structure 200, the first end segment 102 bends at an angle to the longitudinal axis, as shown by step 3(b). In doing this, the tip 112 of the first end segment 102 presses against one wall 202 of the tubular structure 200 and subsequently pushes the body 206 of the first end segment 102 against the opposite wall 204, thereby wedging the first end segment 102 between the walls 202, 204 of the tubular structure 200. The angle at which the first end segment 102 is bent can be adapted according to the diameter of the tubular structure 200. The aim is to bend the first end segment 102 to an extent that it becomes firmly wedged within the tubular structure 200 without exerting an excessive amount of force on the two walls 202, 204. This is particularly useful in applications such as endoscopic procedures where the diameter of the tubular structure 200 varies along its length. Furthermore, the ability to control the magnitude of the anchoring force is particularly useful in preventing damage to the tubular structure 200.

The middle segment 104 then contracts linearly, as shown in step 3(c). As the first end segment 102 is anchored to the tubular structure 200, the contraction of the middle segment 104 pulls the second end segment 106 forward along the length of tubular structure 200 towards the first end segment 102.

Whilst the middle segment 104 is in a contracted position, the first end segment 102 straightens back out and releases its grip on the tubular structure 102, as shown by step 3(d). The second end segment 106 then bends so that it wedges itself between the walls 202, 204 of the tubular structure 200, as shown in step 3(e). As such, the tip 114 of second end segment 106 pushes against one wall 202 of the tubular structure 200, which subsequently pushes the body 208 of the second end segment 106 against the opposite wall 204. As described above, the angle at which the second end segment 106 is bent can be adjusted according to the size of the tubular structure 200. Once the second end segment 106 is anchored between the walls 202, 204 of the tubular structure 200, the middle segment 104 extends back out, thereby driving the first end segment 102 forward, as shown in step 3(f).

This process can be repeated so as to inch the device 1 forward in a way that is similar to the action of a worm. Likewise, the device 1 can move in the opposite direction using the exact same locomotive motion, performed in reverse order.

To increase the distance and the speed at which the device 1 moves in each action, the first and second end segments 102, 106 also contract and extend linearly. That is, when the first end segment 102 is wedged between the walls 202, 204 of the tubular structure 200, both the middle segment 104 and the first end segment 102 contract longitudinally to pull the second end segment 106 forward. Similarly, the second end segment 106 contracts linearly before it anchors itself to the tubular structure 200, and then extends linearly with the middle segment 204 to drive the first end segment 102 forward.

As discussed above, when the segments 102, 104, 106 contract or extend longitudinally, the soft mesh 116 housing the device 1 expands or contracts with this motion. For example, when the middle segment 104 contracts, as shown in steps 3(c) and 3(d), the mesh 116 expands outwards so that the middle segment 104 increases in diameter such that it fills the width of the tubular structure 200. In doing this, the soft mesh 116 increases in stiffness which in turn allows a greater level of friction between the device 1 and the walls 202, 204 of the tubular structure 200. This helps to prevent the device 1 from slipping backwards whilst the first end segment 102 releases its grip in step 3(d) and the second end segment 106 anchors itself in step 3(e). Similarly, such an expansion in the mesh 116 can help to enhance the anchoring of the first and second end segments 102, 106 between the walls 202, 204 of the tubular structure 200. As such, each of the segments 102, 104, 106 are at their largest diameter and stiffest when in a fully contracted configuration.

Conversely, when the segments 102, 104, 106 extend back out, the mesh 116 contracts back to its original configuration such that the segments 102, 104, 106 decrease in diameter and soften. As such, each of the segments 102, 104, 106 are at their smallest diameter and softest when in a fully extended configuration. Consequently, the segments 102, 104, 106 can be made soft so that they easily conform to the curvature of the tubular structure 200 during forward movement, which helps to ensure smooth and unobstructed movement through the tubular structure 200. This is important for ensuring that minimal damage is caused to the inside of the tubular structure 200. This is particularly important in applications such as colonoscopy where the tubular structure 200 is the human colon since it helps to limit the amount of discomfort felt by the patient.

As such, the adaptive mesh 116 allows the properties of the device 1, that is, the stiffness and the diameter of the device 1, to be adjusted on the fly and thus adapted to the surrounding environment. This is particularly useful for tubular structures 200 such as the human colon that do not have a uniform configuration along their length.

Figure 7A:
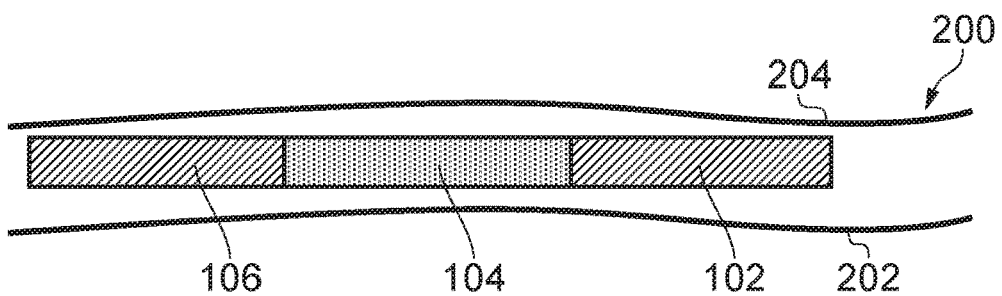
FIGS. 7a-c illustrate the operation of the present invention.
Figure 7B:
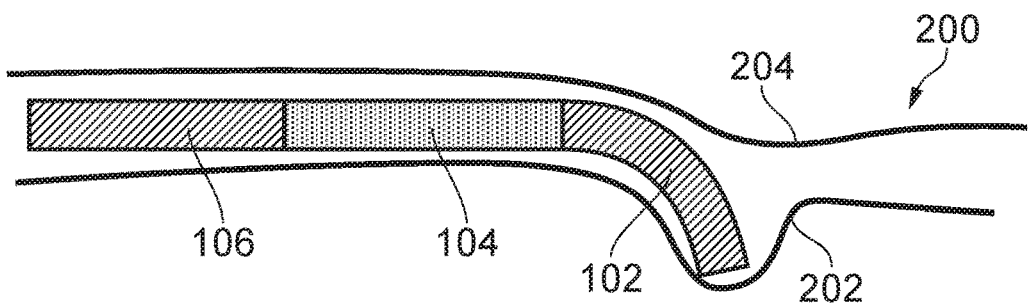
Figure 7C:
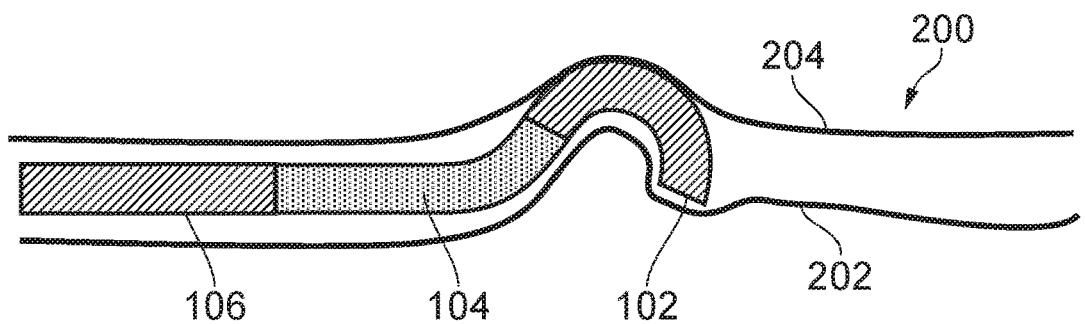

To further improve the anchoring of the device 1, the first and second end segments 102, 106 may be capable of a pinching action, as illustrated in FIGS. 7a-c. FIG. 7a shows the device 1 in its straight configuration within the tubular structure 200. In FIG. 7b, the first end segment 102 is bent at an angle so as wedge or jam itself between the walls 202, 204 of the tubular structure 200, thereby creating a "J"

shape, as described previously. To increase the amount of anchoring, the first end segment 102 may bend further to create a "C" shape and thereby pinch one wall 202 of the tubular structure. This ensures that when the middle segment 104 and/or the second end segment 106 contract longitudinally to inch the device 1 forward, there is no slipping back within the tubular structure 200.

In the above described arrangement, the device 1 comprises three segments, however, the device 1 may comprise two segments. In this respect, the device 1 may comprise the middle segment 104 and one of the end segments 102, 106. That is, a single segment having two or three degrees of freedom and a single segment having a single, linear degree of freedom. In such an arrangement, the device 1 is only capable of moving in one direction within a tubular structure 200 since the direction of motion is determined by the segments 102, 106 that are anchoring the device 1 to the tubular structure 200. Alternatively, the device 1 may comprise two of the end segments 102, 106, that is, two segments having two or three degrees of freedom. Such an arrangement is capable of moving bi-directionally within a tubular structure 200.

In the examples described herein, the device 1 is shown to be moving along a tubular structure 200. However, a person skilled in the art will appreciate that the device 1 is capable of moving along any structure that has two opposing walls between which the end segments 102, 106 can anchor themselves.

As an example, the device 1 may be used as an endoscope for medical screening, as will now be described.

Example

I. Introduction

Colorectal cancer accounts for approximately 10% of all known cancer cases worldwide and is therefore a serious cost to health services[2]. There is evidence to suggest that fear of discomfort is a significant reason for patients not attending regular bowel screenings. As regular screenings are one of the best and most effective methods of preventing bowel cancer[19], the fact that only a little over half of the patients eligible for screening refuse to undergo colonoscopy impairs the effort of screening programs. Finding a more comfortable alternative to traditional push endoscopes could significantly increase participation in regular pre-screenings. Worm-like robots present exactly such an alternative to push endoscopes and research towards improving worm-like robotic endoscope design could have significant impact on people's health and wellbeing. This paper will present a novel design for a soft, multi-segment worm robot.

Recently, a number of worm-like robots have been proposed. An early mesh-based robot consisted of three pneumatically actuated segments specifically intended for use in colonoscopy[14]. Bladder structures based on artificial muscles were inflated to cause an expansion and contraction in a particular segment. Doing this in proper sequence, peristaltic motion was achieved. The device was tested in a rigid plastic pipe to approximate a human intestine and achieved speeds of 5 mm/s. Menciassi et al. produced a device in [15] and [16] that relied on shape memory alloy (SMA) actuators to produce worm-like crawling motion. To ensure that the device would move forward, small hooks were embedded on the outer skin of the robot to increase friction in one direction. While effective during forward movement, this feature does, however, prevent the device from moving backwards. Designs presented in [12] and [13] rely on geared DC motors to actuate linkages between segments, thus producing peristaltic motion. Additionally, an anchoring mechanism was incorporated in the system presented in [13] which allows either the front-most or rear-most segment to increase friction on its surrounding environment. This anchoring mechanism was controllable and the device was able to move both forward and backward. The design presented in [17] consists of a spring-like, soft mesh which is then deformed by a series of SMA actuators. The arrangement of the actuators is inspired by how circular and longitudinal muscle fibres function in common earth worms. Motion is achieved through peristalsis. Additionally, a sensing system was employed to achieve position feedback control of each segment.

A number of commercial alternatives to the traditional endoscope exist. These include the Aeroscope[20], Invendoscope[21, 22], NeoGuide[23, 24] and Endotics Systems[25]. With regard to propulsion method, only Endotics uses an onboard, worm-inspired locomotion system. The Endotics system relies on a technique involving suction and clamping of local colon tissue to anchor either of its two end points. First, the front segment is anchored using suction and clamping. The central segment is then contracted to bring the rear segment forward, where after the rear segment is anchored. The middle segment is then extended and the sequence repeated, driving the device forward, similar to how an inchworm moves. The front segment, equipped with a camera and biopsy tool is able to orient the end segment.

In general, the above research prototypes use segments that have a single degree-of-freedom (DOF). Given that it is necessary to have control of camera orientation and steering in endoscopy, a single DOF system will not be sufficient. The commercial designs (for the most part) allow for camera orientation and steering. Only Endotics relies on force being applied locally to the colon in order to propel the endoscope. The Endotics design uses two separate mechanisms for anchoring and camera orientation/steering. The advantage of the design proposed in this paper is that it uses only one mechanism to achieve both anchoring and camera orientation/steering. Therefore, the complexity of the design is reduced relative to Endotics. Given that endoscopes are required to be very small in diameter, a reduction in complexity can lead to an increase in reliability. Additionally, this device is able to adapt to a varying colon diameter through use of the bending-anchoring method.

II. Design

A. Overview

Figure 4A:
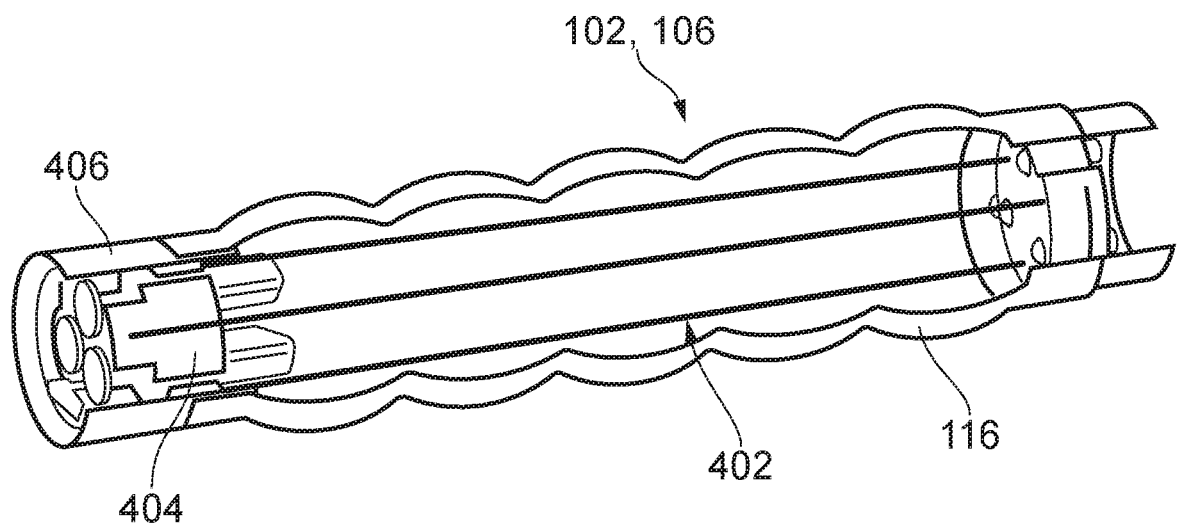
FIG. 4a is a cross-sectional view of a first part of an embodiment of the present invention.
Figure 4B:
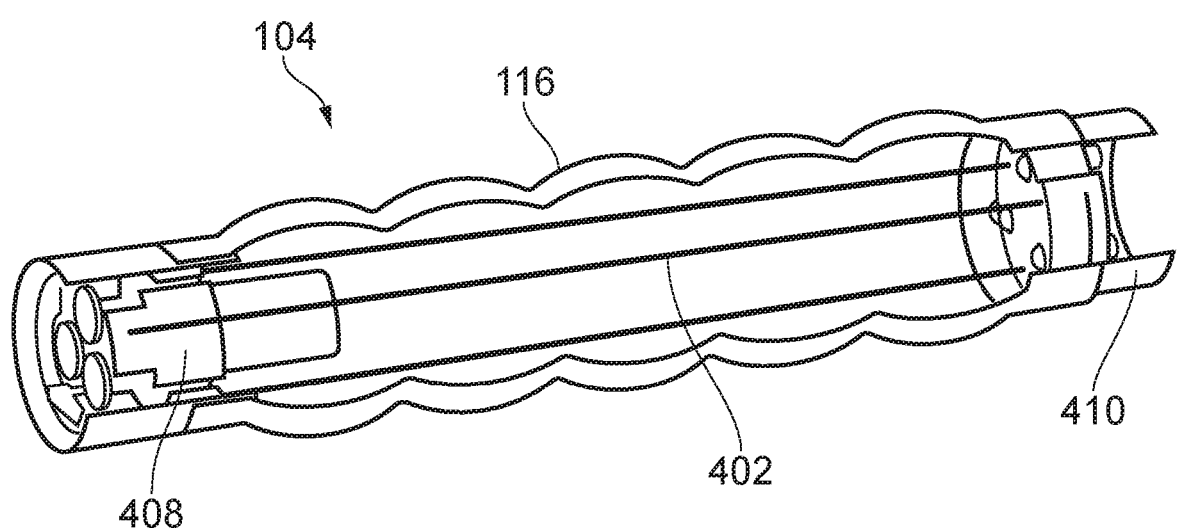
FIG. 4b is a cross-sectional view of a second part of an embodiment of the present invention.

The robot (see FIG. 2, which shows an assembled prototype 1 with an endoscopic camera 108 mounted on one end 112 of the device 1) consists of three separate segments 102, 104, 106. Each segment 102, 104, 106 consists of an elastic mesh structure 116 which is antagonistically driven by tendons 402, as illustrated by FIGS. 4a and 4b. The tendons 402 are wound around pulleys which are mounted on DC motors. As the motors rotate, the lengths of the tendons 402 change, either compressing or extending the mesh body 116. Contraction of each segment 102, 104, 106 is achieved by shortening a tendon 402, thus actively pulling the mesh 116. Extension is achieved by giving the tendons 402 slack and allowing the mesh 116 to passively expand due to its natural elasticity. The front and rear segments 102, 106 are actuated by three motors 404. Therefore, they have one linear DOF to accomplish contraction and extension and two rotational DOFs allowing bending about two axes. The middle segment 104 only has a single, linear DOF for contraction and extension. In this respect, the middle segment 104 is actuated by a single motor assembly 408. The design is modular—segments can be fitted together in any order and motor housings can be swapped between meshes at will. With this in mind, the fundamental structure of any given segment 102, 104,106 is the same. To this end, the end segments 102, 106 may comprise female collars 406 arranged to cooperate with male collars 410 on the middle segment 104. This basic structure is shown in FIGS. 4a and 4b, which illustrate cut-away sections of computer models of the 3-DOF segment (4a) and the 1-DOF segment (4b).

Figure 5:
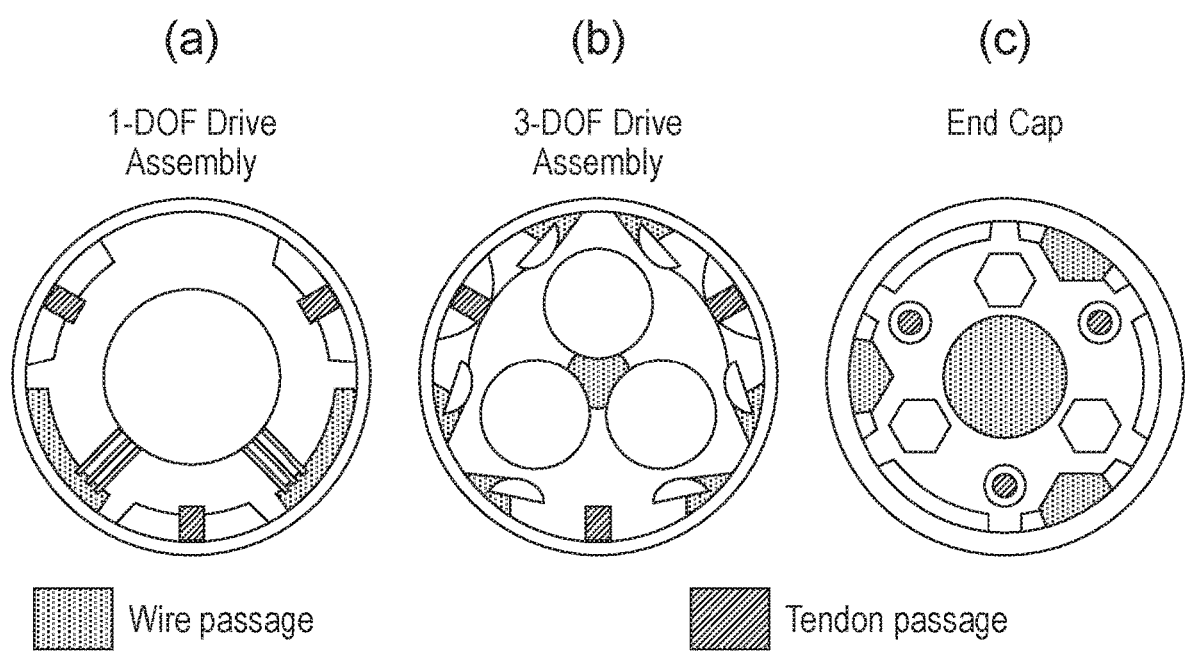
FIGS. 5a-c are cross-sectional views of three parts of an embodiment of the present invention.

In order to evaluate the system's ability to function as an endoscope, a miniature USB camera (6 mm diameter, 640× 480 resolution) with illuminating LEDs was mounted on the end of the prototype. The final prototype was approximately 50 cm in length. The camera cables were passed through the drive assemblies using specially designed passages (see FIG. 5). FIG. 5 shows the front view of the two drive assemblies 204, 208 and the end cap 212, showing where the wires and working channels could be passed through. The sizes of these passages can be easily increased in the future. The camera is fixed in a plastic housing, attached at the tip of the front segment, where it would be possible in the future to mount additional equipment such as a biopsy tool.

The body of the robot is comprised of the polyethylene terephthalate (PET) mesh material proposed in[26]. The mesh has been heat treated around a specially designed mould, creating a ribbed structure. The flexible section of each mesh is approximately 80 mm long and has a stiffness equal to 0.223 N/mm over a strain range between 0 to 50%, which was sufficient for this design. The outer mesh could be made water tight and disposable to ensure sterilisation, allowing the drive assemblies to be reused with minimal cleaning and sterilisation effort.

The outer diameter of all of the collars is 26 mm. The maximum outer diameter of the mesh when uncompressed is approximately 31 mm and 35 mm when compressed. Given that the mesh is a soft material, these diameters are of less concern compared to that of the rigid collar/drive assemblies. As the colon is around 26 mm in diameter at its narrowest[27], however, the device's diameter will need to be reduced in future design iterations. Significant diameter reductions can be achieved by redesigning the sensing system (see Section III-B).

B. Locomotion Strategy

The proposed locomotion strategy (see FIG. 3, which illustrates a single iteration of the proposed locomotion sequence) takes advantage of the end segments' ability to bend in order to selectively increase frictional forces between the colon wall and the skin of the robot. As it is assumed that the device will always be travelling in a tubular environment, bending one segment to a sufficiently large angle will "jam" it into place. As the tip of the bending segment presses against one side of the colonic wall, the curved middle section of the segment is pressed against the opposite wall. As the mesh is compliant, it will deform, avoiding damaging the colon and increasing the friction between the colonic wall and the bent segment, thus anchoring it into place. A primary advantage of this method is that the bending angle of the segment can be adjusted to adapt to changing colon diameters. As the diameter of the human colon varies significantly depending on location in the colon[26], this adaptability is highly useful for endoscopy.

Figure 6:
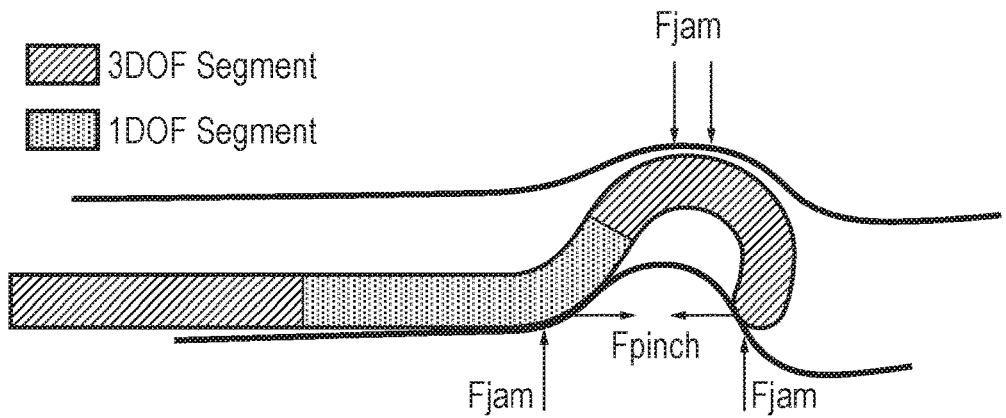
FIG. 6 illustrates the operation of the present invention.

In addition to the "jamming" method, one of the 3DOF segments can be bent to a sufficiently large angle that will allow the worm to also "pinch" the lumen (see FIG. 6, which illustrates the end segment's ability to "pinch" the lumen as well as jam), pressing a small section of the lumen between either end of a 3DOF segment. This further increases the device's ability to anchor itself in the lumen.

Forward motion is achieved by having only one of the end segments anchored. The middle segment is then able to move the unanchored end segment relative to the anchor by contracting or extending. Thus, when done in the correct sequence, forward or backward locomotion may be achieved. Additionally, as each of the end segments can bend, they are able to actively steer the device around turns and control the orientation of a camera mounted on the end. Given that the human colon can be highly tortuous[26], this ability to steer is critical.

C. Locomotion Analysis

Figure 8:
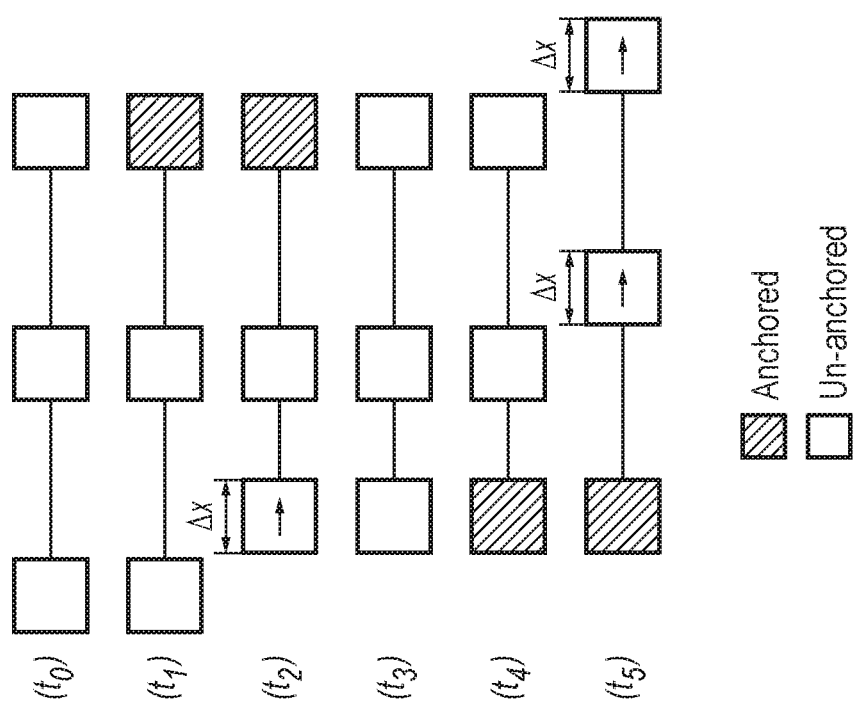
FIG. 8 is a block diagram illustrating the operation of the present invention.

In each iteration of the proposed locomotion sequence, the theoretical distance by which the tip of the robot will advance is equal to the contraction distance of the middle segment $\Delta x_{e,ideal}$. This is illustrated in FIG. 8, which provides a simplified diagram of the locomotion sequence. Additionally, the total time taken for each iteration is equal to $\Delta t_{tot}$. Hence, the ideal speed of the robot may be expressed as $$v_{ideal} = \frac{\Delta x_{e,ideal}}{\Delta t_{tot}} \tag{1}$$

Figure 9:
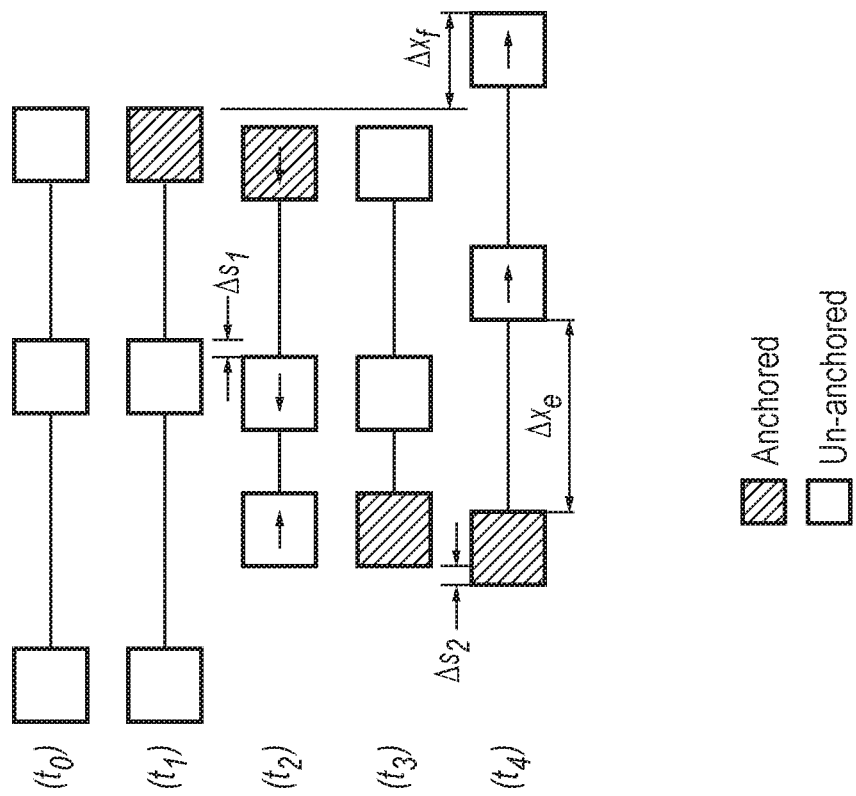
FIG. 9 is a block diagram illustrating an alternative operation of the present invention.

From equation (1), it is clear that to increase speed either $\Delta x_{e,ideal}$ must be increased or $\Delta t_{tot}$ must be decreased. While simply making each segment move as fast as possible would increase the speed, modifications to the sequence itself could also potentially improve performance. The sequence shown in FIG. 8 only permits a single segment to move at any given time. By allowing segments to move simultaneously, stages of the original sequence may be skipped, and thus decrease $\Delta t_{tot}$. This is achieved by combining stages of the basic sequence so that segments move simultaneously. For example, if the anchoring and unanchoring stages were performed simultaneously for the two end segments, then only four stages would be required, as opposed to six. In other words, the stages at $t_e$ and $t_s$ are removed. This is shown in FIG. 9, which shows a diagram of a single iteration of the improved locomotion sequence where non-idealities occur. Here, $\Delta s_i$ refers to the distance slipped by, and $\Delta x_e$ denotes the actual extension distance of the middle segment.

In order to have a clearer understanding of how the device performs, the efficiency of locomotion may be defined as $$\eta_{loc} = \frac{v_{real}}{v_{ideal}} \tag{2}$$

where $\eta_{loc}$ is the locomotive efficiency and $v_{real}$ is the measured speed of the device. There are two primary ways in which locomotive efficiency could drop, as illustrated in FIG. 9. Firstly, the middle segment could fail to extend completely due to external friction. Since it is not possible to directly control the extension of the mesh (it is only possible to "allow" it to passively extend), it is possible that this middle segment will not extend completely during operation. Secondly, the anchoring force could be insufficient on one of the end segments and result in an anchored segment slipping. Thus, it is possible to define the actual distance moved forward each iteration $\Delta x_f$ as $$\Delta x_f = \Delta x_e - \Delta x_s \tag{3}$$

where $\Delta x_s = \Delta s_1 + \Delta s_2$. The real velocity may then be defined as $$v_{real} = \frac{\Delta x_e - \Delta x_s}{\Delta t_{tot}} = \frac{\Delta x_f}{\Delta t_{tot}} \quad (4)$$

With this, additional locomotive efficiencies may be defined in order to better understand the behaviour of the device. Substituting equations (1) and (4) into (2) yields $$\eta_{loc} = \frac{\Delta x_f}{\Delta x_{e,ideal}} = \frac{\Delta x_e}{\Delta x_{e,ideal}} \cdot \frac{\Delta x_f}{\Delta x_e} = \eta_e \eta_a \quad (5)$$

where $$\eta_e = \frac{\Delta x_e}{\Delta x_{e,ideal}} \text{ and } \eta_a = \frac{\Delta x_f}{\Delta x_s}.$$

The expansion efficiency $\eta_e$ measures how much of the theoretical expansion is achieved. The anchoring efficiency $\eta_a$ measures how effectively the system is able to anchor during the locomotion sequence. Thus, two separate quantities can be measured to evaluate the two primary performance aspects of the device.

D. Sequence Implementation

In order to easily implement the locomotion sequence, it is useful to split each sequence into two separate parts: anchoring/unanchoring and contraction/extension. It is reasonable to assume that each individual part will always take the same time to perform. Also, regardless of the details of the locomotion sequence, there will necessarily have to be a contraction stage and an extension stage for the middle segment in order to produce forward movement. Hence, equation (1) may be rewritten as $$v_{ideal} = \frac{\Delta x_{e,ideal}}{N_{anch} \Delta t_{anch} + 2\Delta t_{con}} \quad (6)$$

where $N_{anch}$ refers to the number of anchoring/unanchoring stages present in the sequence, $\Delta t_{anch}$ refers to the time taken for a single anchoring/unanchoring stage and $\Delta t_{con}$ refers to the time taken for a single contraction/extension stage. In equation (6), only $N_{anch}$ is dependent on the design of the locomotion sequence itself. The variables $\Delta x_{s,ideal}$, $\Delta t_{con}$ and $\Delta t_{anch}$ are dependent on the limitations of the actuators and hardware used in the device. Therefore, $N_{anch}$ is the defining variable which may identify a given locomotion sequence. In this case, $N_{anch}=2$.

III. Design Features

A. Actuator Selection

Miniature DC motors were selected to actuate the robot due to their wide availability and low cost. The Precision Microdrives 206-10C was selected to drive the 3-DOF segment and the larger Precision Microdrives 212-103 12 mm DC motor was chosen for the 1-DOF segment. The relevant properties of these motors are summarised in Table 1.

TABLE 1

Summary of relevant motor properties

| Property | Motor 3-DOF | Motor 1-DOF |
|---|---|---|
| Rated Voltage/V | 3 | 3 |
| Diameter/mm | 6 | 12 |
| Length/mm | 24.0 | 20.8 |
| Rated Torque/mN-m | 10 | 40 |
| Rated Speed/rpm | 37 | 22 |
| Pulley Radius/mm | 2 | 5 |
| Rated segment contraction speed/mms$^{-1}$ | 7.75 | 11.5 |
| Rated segment contraction distance/mm | 67 | 36 |

With these values, the parameters of the locomotion sequence were selected as follows: $\Delta x_{e,ideal}=45$ mm, $\Delta t_{anch}=3$ s and $\Delta t_{con}=4$ s.

B. Sensing

Figure 10:
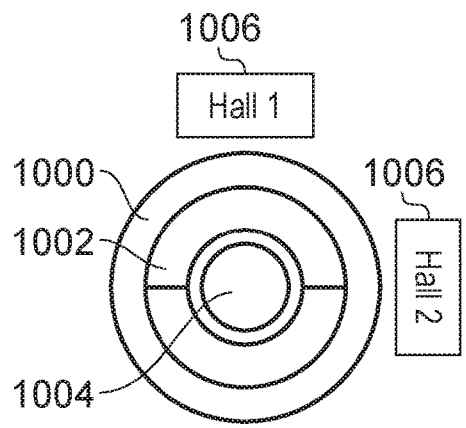
FIG. 10 illustrates a sensor system used in the present invention.

In order to implement feedback control on each tendon, a Hall Effect-based sensor system was used. The principle is shown in FIG. 10, which shows a view of the underside of a pulley to illustrate the sensing system's functionality. A ring-shaped magnet 1002, diametrically magnetized, was embedded in the bottom of each pulley 1000 mounted on the shaft 1004 of each DC motor. Two Hall Effect sensors 1006, 1008 were placed 90° apart around the perimeter of the pulley 1000. The signal of each sensor 1006, 1008 varied sinusoidally with the pulley's angular position. As the two sensors 1006, 1008 were physically 90° apart, the sinusoidal sensor signals were also 90° out of phase. After linearly mapping the two signals such that they each had a value in the range [1, −1], the angle of the pulley 1000 could be computed using:

$$\theta(t) = A \tan 2[h_1(t), h_2(t)] \quad (7)$$

where $h_1(t)$ and $h_2(t)$ are the Hall Effect sensor readings after mapping. With the absolute angle of the pulley 1000 known at any time, it was possible to calculate the length of each tendon with knowledge of some initial tendon length and the associated pulley angle:

$$L(t) = L(0) + [\theta(t) - \theta(0)] \cdot r_{pulley} \quad (8)$$

Figure 11:
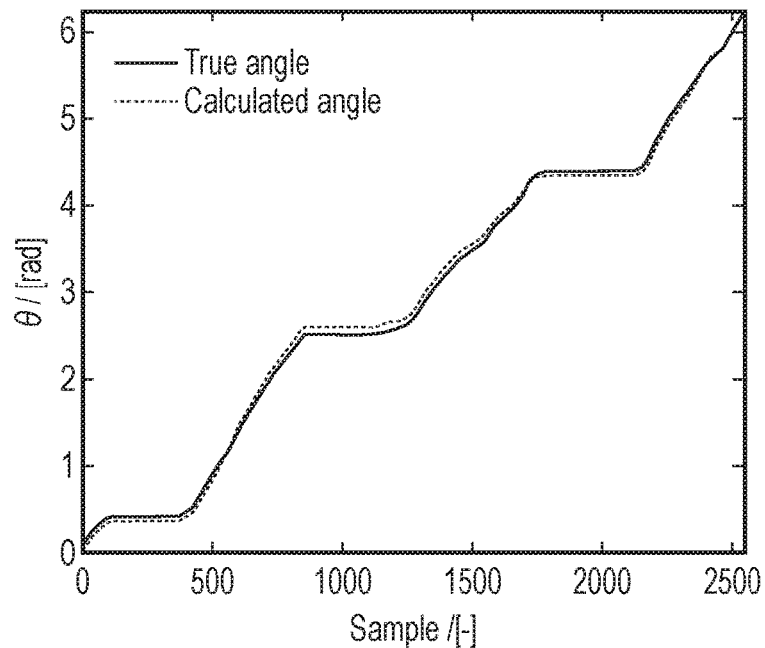
FIG. 11 is a graph illustrating the efficacy of the sensor system.

To evaluate the sensing system, a potentiometer was rigidly attached to a pulley to provide a reliable measurement of the pulley angle. A comparison between the two readings is shown in FIG. 11, which shows a plot of comparison between the angle measured with the potentiometer (the "True angle") and the angle measured with the Hall Effect sensing system (the "Calculated angle").

C. Control

Figure 12:
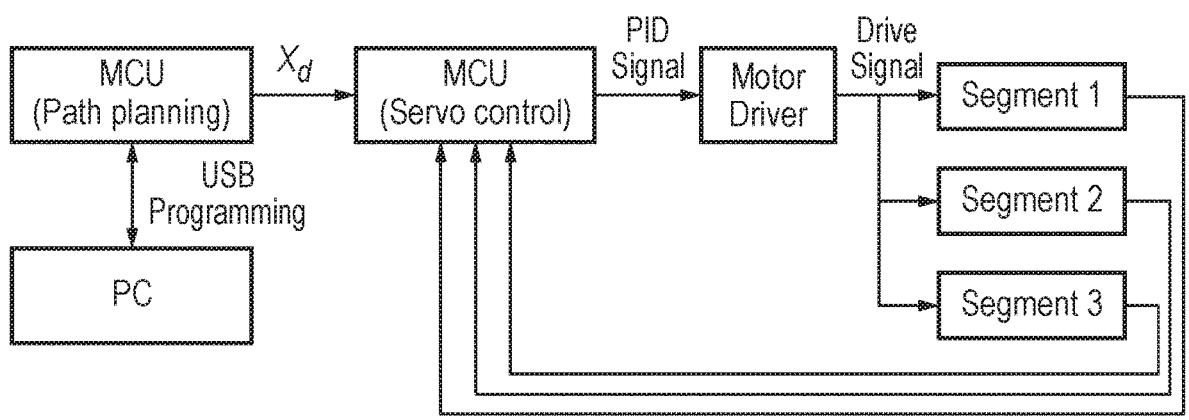
FIG. 12 is block diagram of the control system used in the present invention.

A simple PID controller was chosen to control the length of each tendon. This was implemented on a single microcontroller (MCU) board which would process the signals from the Hall Effect sensors in each segment and compute the PID control output. A secondary path planning MCU would compute high level path control information and send this to the other MCU via I$^2$C bus. This is shown in FIG. 12, which provides a block diagram of the control system implemented.

IV. Experiment

Two experiments were carried out. Firstly, the middle segment step response was evaluated to investigate the effectiveness of the contraction/extension movement. Secondly, the prototype was run through a simulated colon.

A. Step Response

In order to ensure that the middle segment was accurately contracting, a simple step response test was carried out on the fully assembled prototype. This involved commanding the central segment to contract from an un-extended state to a given new length and then back to its original length. A vision system was used to evaluate the true position of a marker on the end of the central segment.

Figure 13:
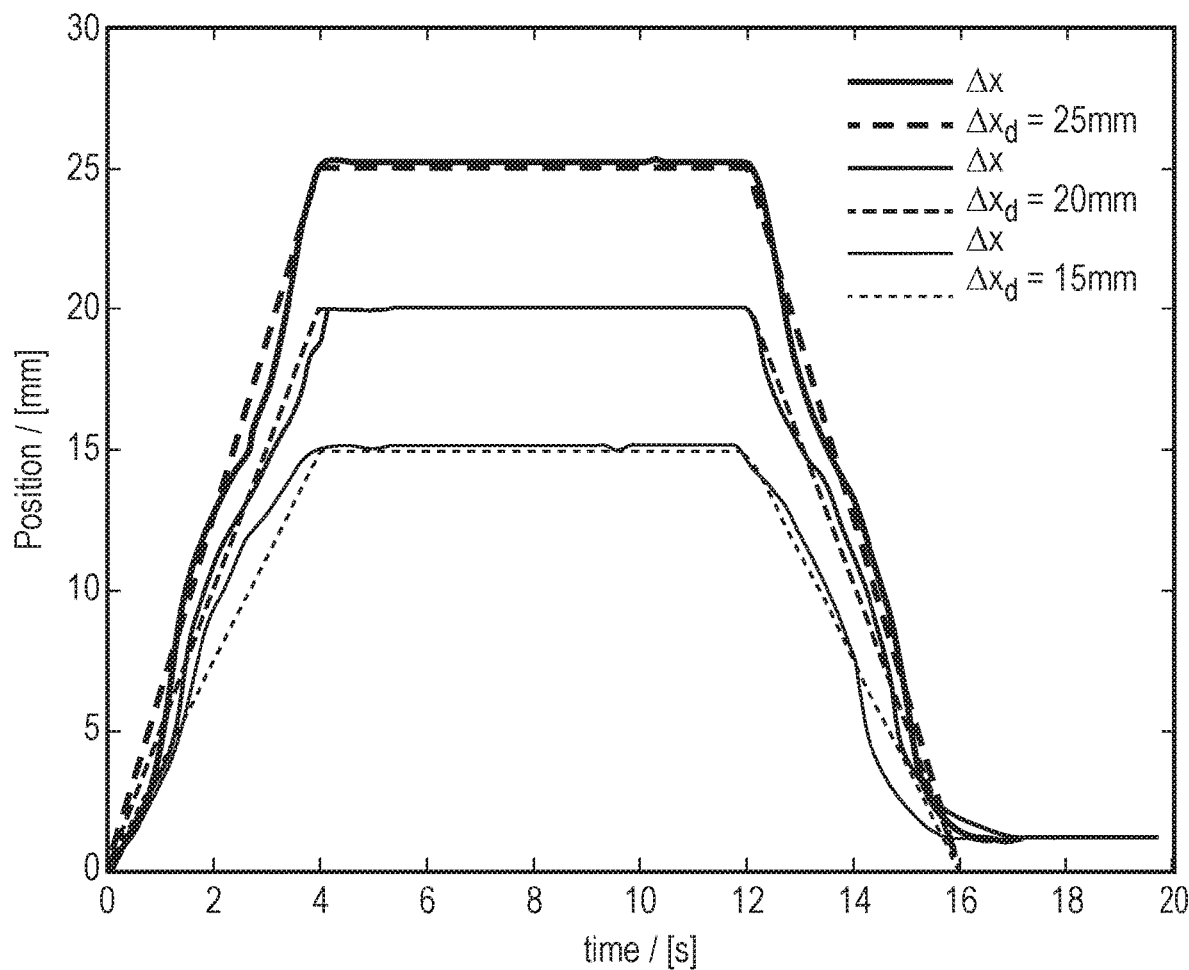
FIG. 13 is a graph illustrating the step response of the present invention.

The results of this are shown in FIG. 13, which shows the step response of the middle section for various contraction distances. The dashed lines indicate the demanded path while the solid lines indicate the actual position of the end of the segment. It is clear from this that the system shows some problems with regard to tracking a dynamic path. The system is, however, sufficiently accurate in reaching the final target position. Upon extending back to its original length, on the other hand, the segment does not reach its original position. This is most likely due to the low restoring forces present at low extensions which are insufficient to overcome friction.

B. Simulated Colon

The prototype was run through a simulated colon. A sheet of flexible plastic "bubble wrapping" was rolled into a tube to create a simulated colon. This was selected as an appropriate experimental simulacrum primarily due to its soft and compliant properties. The tube was approximately 50 mm in diameter and 1200 mm long. Its internal surface was dry and smooth. The tube was laid on a bench on top of a number of additional layers of bubble wrapping. In order to better account for the fact that the colon is only partially hung and is therefore mobile in the abdominal cavity, only one end of the tube was fixed to the table, while the other was allowed to move freely. The robot would start a run at the free end of the tube and move toward the fixed end.

The bending angles of the two end segments were chosen by trial and error while testing in the simulated colon. It was found that with all segments straight and extended, the robot was subject to around 1.1N of static frictional force. With the front segment bent, this frictional force increased to around 2.0N, thus validating that the segment jamming strategy could work in a real colon.

Figure 14:
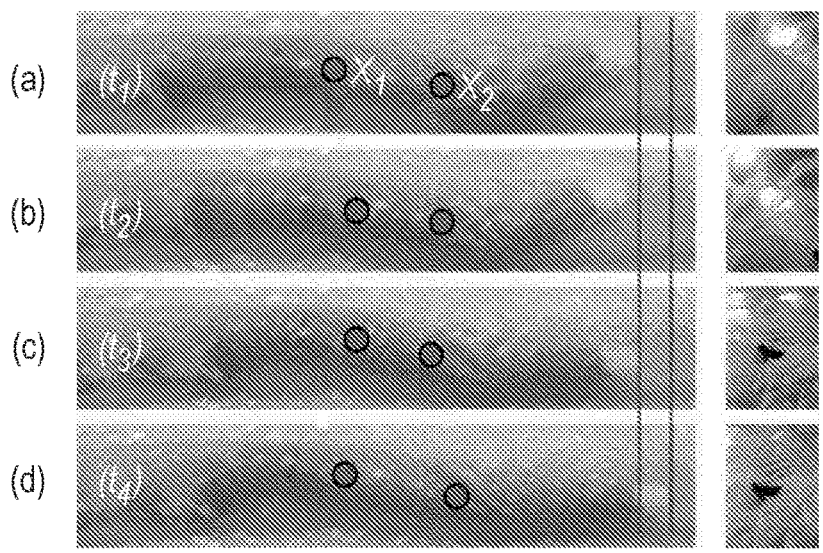
FIG. 14 is a time lapse sequence of an embodiment of the present invention in use.
Figure 15:
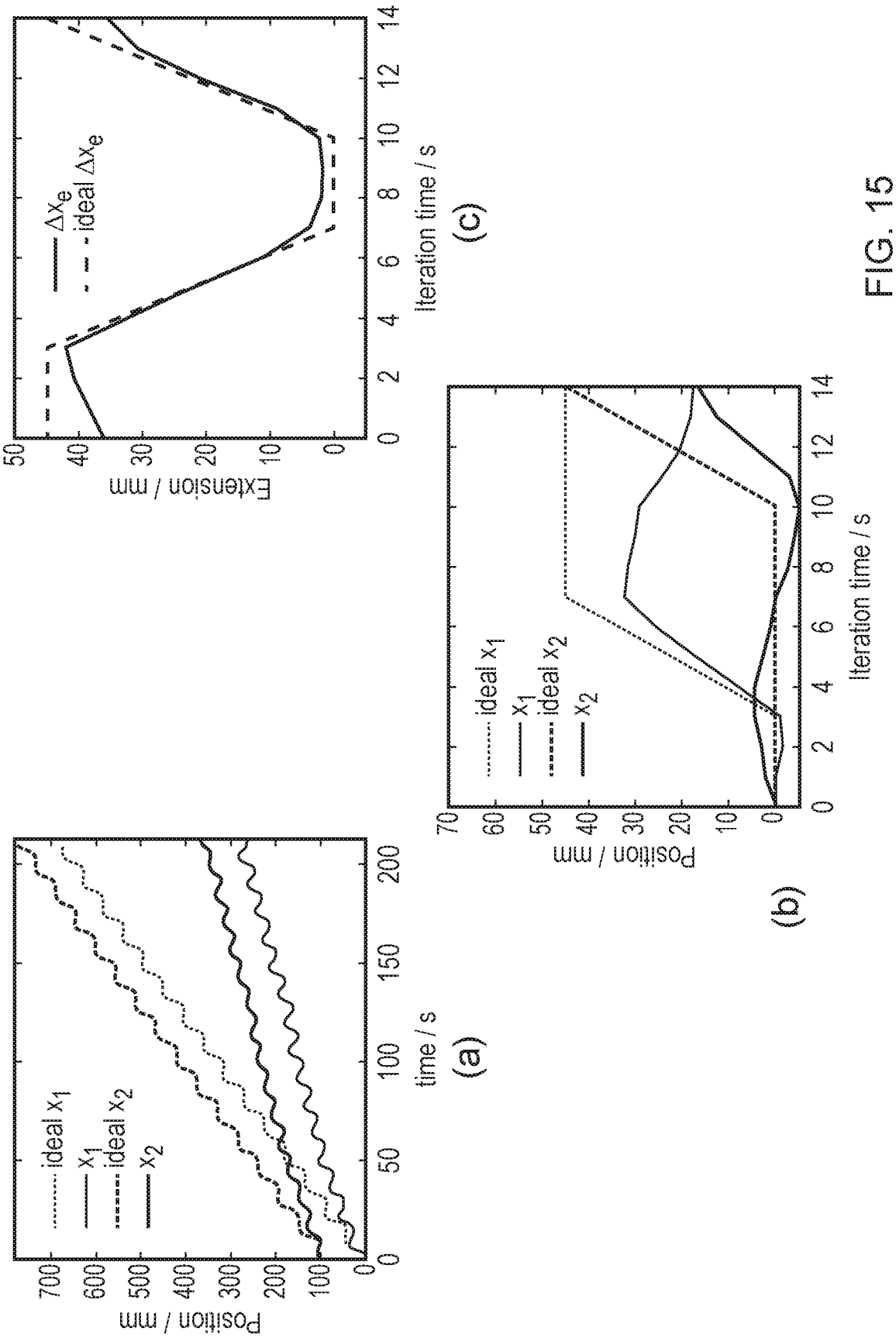
FIGS. 15a-c are graphs showing the results of tests used to assess the efficacy of the present invention.

A time-lapse sequence of a single iteration of the locomotion sequence is shown in FIG. 14. The position of two markers on the body of the worm were used to calculate the locomotion parameters discussed in section II. In FIG. 14, the positions of the markers are indicated as dots and a corresponding view from the on-board camera is provided to the right of each picture. A plot of the position of the rear and front points of the middle segment ($x_1$ and $x_2$ respectively) is shown in FIG. 15 (a). FIG. 15 (a) shows the positions over the whole experiment in comparison to their theoretical positions.

The average speed of the device was calculated by measuring the total distance traveled and the total time taken for the worm to reach its final position. This then allowed $\eta_{loc}$ to be calculated with knowledge of the ideal speed discussed previously.

The raw data was then separated to allow for each iteration to be analysed individually. Data from each individual iteration was then compared at fixed 1 s intervals. With this data, it was possible to produce an average trajectory for a given marker during a single iteration. These results may be seen in FIGS. 15 (b) and (c). FIG. 15 (b) shows the average position of the middle segment during one sequence iteration. For simplicity, the results were normalised in order to shows that the middle segment always starts at zero. FIG. 15 (c) shows the average extension of the middle segment over a single sequence iteration.

The extension at each iteration was calculated by noting the initial distance between $x_1$ and $x_2$, denoted as $\Delta L_0$. Then, for each iteration, the total extension for each iteration was calculated according to $$\Delta x_e = x_2(t_4) - x_1(t_3) - \Delta L_0 + \Delta x_{e,ideal} \quad (9)$$

where $t_3 = 10$ s and $t_4 = 14$ s relative to the beginning of each iteration respectively. Also, $\Delta x_{e,ideal}$ was added such that when the segment had contracted, a value of zero would be obtained and if a full extension occurred, a value equal to $\Delta x_{e,ideal}$ would be obtained. The results of the analysis on the average trajectories are shown in Table 2.

TABLE 2

| Average locomotion test results | | | | | | |
|---|---|---|---|---|---|---|
| $v_{real}$/ mms$^{-1}$ | $\Delta x_s$/ mm | $\Delta x_e$/ mm | $\Delta x_s$/ mm | $\eta_{loc}$ | $\eta_e$ | $\eta_a$ |
| 1.21 | 16.99 | 39.70 | 22.71 | 0.38 | 0.88 | 0.43 |

V. Discussion & Conclusion

The prototype performed reasonably well overall. With the average speed of 1.21 mm/s found in the experiment, the device would be able to move from one end of the average human colon with a length of 1850 mm[17] to the other in under 30 minutes (or just under an hour in order to complete both forward and return journeys). This is consistent with the existing technology of flexible endoscopy, which entails approximately 45 minutes for an entire procedure[28], but with the advantage of potentially less pain, if no pain at all—even without sedation, which is required during standard flexible colonoscopy.

The extension efficiency was reasonably high. Looking between t=10 s and t=14 s in FIG. 15 (c), the segment is able to extend most of its desired length, but as the compressive energy is reduced, external friction begins to play a larger role and slows down the rate of extension. Therefore, it is not able to complete the full extension during the allocated 4 s.

As a result, during the first anchoring/unanchoring stage of each sequence, some extension would occur in addition to that which had happened during the previous sequence. This can be seen from t=0 s to 3 s in FIGS. 15 (b) and (c). It can also be seen in FIG. 15 (b) that this unintended extension would allow for some forward motion for but also some backward motion for $x_s$, as neither end segments are fully anchored during this period. In order to ensure that the extension only occur within the allocated time frame, using a stiffer mesh for the central segment would mean that more compressive force would be available to overcome external friction.

Slipping was observed as occurring on both of the end segments while they were anchored. To mend this, larger bending angles could be employed or the surface qualities of the mesh could be altered to increase grip while bending.

An experiment was carried out to evaluate the device's ability to turn. Due to the limited torque available from the motors used in the 3-DOF segments, a maximum bending angle of 90° was available. It was found that the robot was able to navigate a bend of approximately 70°. Beyond this, friction becomes too great. It is therefore reasonable to conclude that the tip must be able to bend at an angle greater than the largest angle expected to be encountered. A critical improvement of the design would be to allow the front segment to bend 180°. This can be achieved by sourcing more powerful actuators, making the mesh less stiff, or increasing the friction generated by an anchoring segment.

With regard to the design of the robot itself, a number of issues must be addressed in the next iteration of the design. The device must be miniaturised and working channels for air and water must be incorporated. Additionally, as the maximum diameter of the colon in which the device can anchor is primarily a function of the length of the two end segments, more investigation is required to determine the ideal lengths required for each segment.

Regarding the simulated colon, some of the key properties of the colon were replicated: it was collapsed, partially hung and compliant. The elasticity of colon tissue, however, is significantly greater than the material used in the experiment[29]. It is expected that in order to tackle these challenges, the interaction between each of the 3-DOF segments and the colon wall during anchoring must be examined in detail. This will allow for an optimised anchoring system and will be the topic of future research.

In future, a control interface will also be required. A control interface will be developed as the full details of the locomotion sequence are established.

In conclusion, a novel design for a robotic mesh worm was presented for use in colonoscopy. The device employs a novel new anchoring technique which allows the device to achieve forward locomotion, camera orientation and anchoring with only a single mechanism. A theoretical framework through which to understand the locomotive performance of the device was established. The device was fabricated and tested in a simulated colon, achieving an average speed of 1.21 mm/s, approximately 38% of the theoretical maximum. In the future, the theoretical framework will be utilised to identify design improvements which will allow the device to be more efficient and achieve higher velocities.

Further developments and implementation considerations will now be described.

Shape and Contact Force Estimation

In the devices described above, two feedback systems are employed in the end segments 102, 106 with 3 degrees of freedom; tendon length sensing and motor torque sensing. On their own, each of these feedback systems can be used to estimate the shape (i.e. the curvature and length) of a given segment. Combining these approaches can increase the accuracy of the shape estimation. This is critical to improving the ability to estimate the interaction forces between a segment 102, 104, 106 and the environment around it and will therefore improve the safety of the device when deployed in a human colon.

Skin Friction Mechanism

The fiction interaction between the environment and the mesh body 100 of the device 1 is a fundamental part of how it is able to move. Therefore, it is important to have control over this interaction so as to increase friction at some times, whilst decreasing friction at other times. In the arrangements described above, the friction is adjusted by how hard the segment 102, 104, 106 is pushing against a surface. However, it is possible to allow the inherent frictional properties of the mesh skin 116 to change depending on the shape of a bending segment 102, 106. The friction interaction can then be controlled using these two methods. This helps to minimise the amount of force applied to the environment while maximising the amount of friction. This also helps to limit any damage to environment in which the device is deployed, which is useful for improving the safety of the device when used for a colonoscopy.

Hydraulic Actuation, Cost Reduction and Miniaturization

In some arrangements, the device may be actuated hydraulically rather than with DC motors as described above. This will reduce the cost of manufacturing the device such that the device itself (not including external control equipment) may be disposable and single use, thus simplifying use in a clinical setting. Hydraulic actuation also provides pressure feedback, which would allow for force estimation, and volumetric feedback, which would allow for shape sensing. Additionally, a hydraulic system would allow the size of the design to be decreased, potentially allowing it to be used in other clinical procedures involving smaller vessels, such as upper endoscopy or bronchoscopy.

On-Board Biopsy Tool

The device may also include an on-board biopsy too to take tissue samples. This is opposed to a traditional biopsy tool which is fed through a pipe from the outside to protrude from the distal end of the endoscope. As such, an on board biopsy tool will help to keep the diameter of the device as small as possible.

Optimum Tool Orientation and Force Configuration

In order to optimise the available force of any end-mounted tool, optimum configurations of the end segments 102, 106 will be studied. This will examine what shapes of the end segments will allow for both optimum view of the work space while maximising the available force which could be applied with an end-mounted tool. This is possible due to the reconfigurable nature of the device's shape.

Shape and Contact Force Estimation

Further developments in shape and contact force estimation will now be described in more detail.

Shape Estimation

Figure 16:
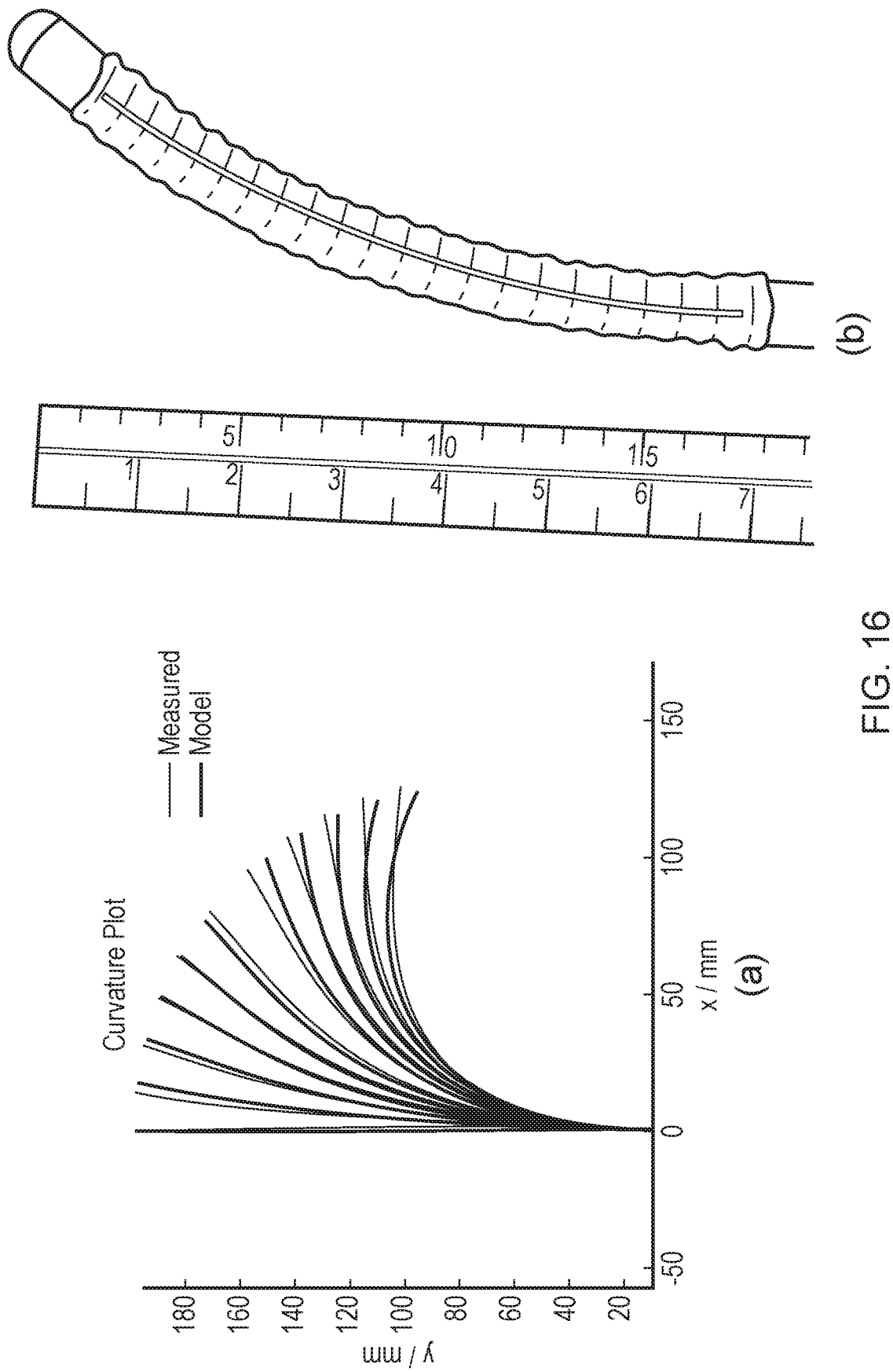
FIG. 16a is a graph illustrating shape estimation using embodiments of the present invention.
FIG. 16b illustrates shape estimation using embodiments of the present invention.

To estimate the shape of a single segment 102, 104, 106 during bending, it is assumed that the segment 102, 104, 106 forms part of an arc with constant curvature. Using knowledge of the length of each tendon 402, a reasonable approximation of the segment's shape in three dimensional space can be made. FIGS. 16a and 16b show a comparison between the estimated shape from the model and the actual measured shape of a segment during bending.

This approximation can be improved by using a more complex model which accounts for the tension in each tendon 402. This, however, introduces a significant number of additional parameters which greatly affect the accuracy of the model and are both difficult to measure and prone to changing non-linearly during bending. For example, the flexural stiffness of each segment 102, 104, 106 is required to estimate the restoring force which is exerted by the segment body on the tendon 402 as a result of bending. The elastic mesh used in the prototypes will change its diameter as it is compressed. As flexural stiffness depends on the diameter of the structure under bending (which also introduces local compression), therefore the flexural stiffness changes as bending occurs.

The accuracy of the shape estimation using only tendon lengths is sufficient to allow it to be used in other calculations (as shown in FIGS. 16a-b), such as contact force estimation, which will be discussed in more detail below.

The shape of a segment 102, 104, 106 is estimated using the tendon lengths. This will assume that the segment 102, 104, 106 has a constant curvature. The exact method of estimation will depend on the geometry and arrangement of the segment 102, 104, 106 and the actuating tendons 402. In this case, the segment 102, 104, 106 was assumed to be a long cylinder of constant diameter and the three tendons 402 equally spaced 120° apart.

The tendon 402 arrangement inside of a cylindrical segment 102, 104, 106 is shown in Error! Reference source not found. FIG. 17$a^{30,31}$, and the variables describing the shape of a single segment 102, 104, 106 in 3D space is shown in FIG. 17$b^{32}$.

Using well-known models[31,32], it is possible to calculate the three segment variables θ, φ and s from knowledge of the three tendon lengths, $l_1$, $l_2$ and $l_3$ (i.e the forward kinematics), using the following equations:

$$s = \frac{l_1 + l_2 + l_3}{3} \tag{10}$$

$$\theta = 2s \frac{\left(\sqrt{l_1^2 + l_2^2 + l_3^2 - l_1 l_2 - l_2 l_3 - l_1 l_3}\right)}{d(l_3 + l_2 + l_3)} \tag{11}$$

$$\phi = \tan^{-1}\left(\frac{\sqrt{3}}{3} \frac{l_3 + l_2 - 2l_1}{l_2 - l_3}\right) \tag{12}$$

Where d is the radial distance from the centre of the segment to the location of the tendon.

Similarly, the inverse kinematics are given by:

$$l_1 = s - \theta d \sin \phi \tag{13}$$

$$l_2 = s + \theta d \sin\left(\frac{\pi}{3} + \phi\right) \tag{14}$$

$$l_3 = s - \theta d \cos\left(\frac{\pi}{6} + \phi\right) \tag{15}$$

Thus, with knowledge of the tendon lengths from on-board sensing equipment, the shape of a segment 102, 104,106 can be estimated. This model does not include any dynamic or gravity effects, which will affect the accuracy of the result. In general, though, if the mass of each segment is low and the movements are slow, then the above model produces adequate results.

Contact Force Estimation

Figure 18A:
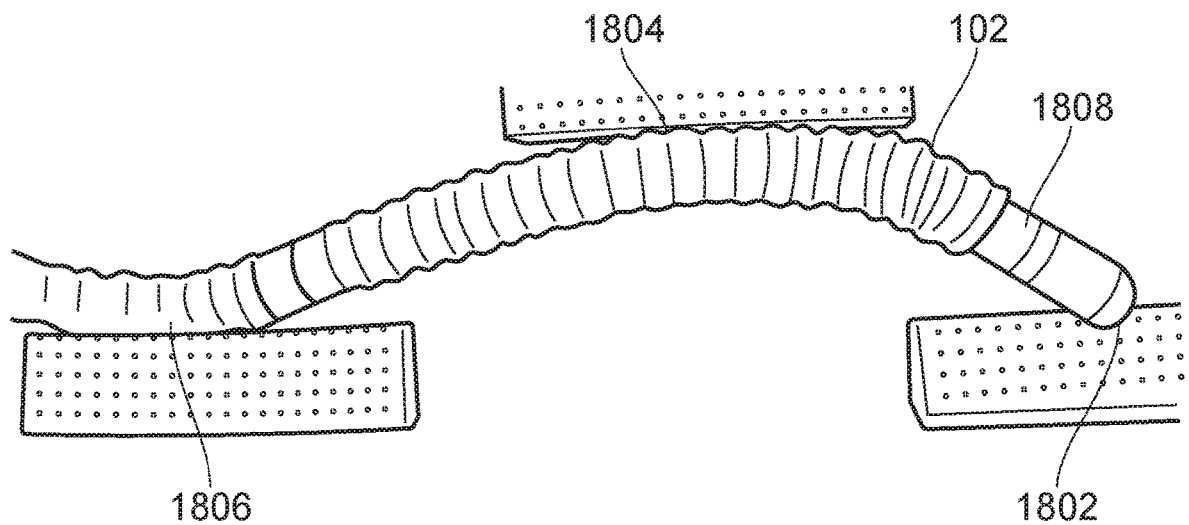
FIGS. 18a-b illustrate contact force estimation using embodiments of the present invention.
Figure 18B:
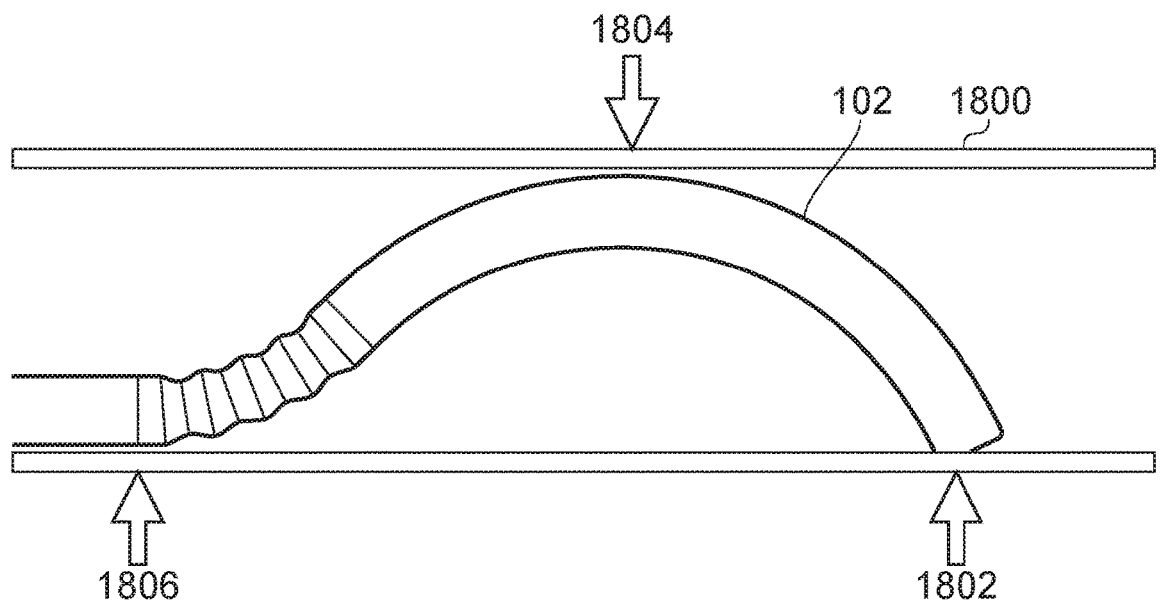

The contact forces exerted by a segment 102, 104,106 on its environment when connected to a series of other segments 102, 104,106 (as in the proposed 3-segment endoscope design) are critical to understanding how well the segment 102, 104,106 anchors itself to the environment. As an example, a single bending segment 102, situated at the distal end of the endoscope, is modelled as being in contact with a compliant surface. In this respect, FIGS. 18a and 18b illustrate a configuration of a segment 102 when anchoring in an enclosed environment 1800, and how these forces are modelled and separated into three points of contact, 1802, 1804, 1806.

The tension in each tendon 402 is what creates the contact forces. Knowledge of this tension is therefore critical to accurately estimating the contact forces. While current measurements from the DC motors 404 used to actuate the tendons 402 can in theory be used to calculate the tensions, this is problematic in practice due to high-ratio gearboxes. Therefore, to attain a better tension measurement, a load cell 1808 was designed using strain gauges and placed at the end of the segment 102. Thus, a direct measurement of the tension was available.

In order to calculate the three reaction forces, first the shape of the segment 102 must be made available using the method described above.

Using the coordinate system shown in FIG. 17a, the distance between the segment centre and the location of the $i^{th}$ tendon can be expressed as a vector $d_i$. The tension on the $i^{th}$ tendon at the $j^{th}$ position on the segment with magnitude $t_{j,i}$ can also expressed as a vector $t_{j,i}$ in the coordinate system in FIG. 17a. In this case, the tension is acting at both ends of the segment 102. Therefore, the tension of each tendon 402 acting at the rear and front ends will be denoted $t_{rear,i}$ and $t_{front,i}$ respectively. With this, the moments at each of these ends ($m_{rear}$ and $m_{front}$) can be calculated with:

$$m_j = \sum_i d_i \times t_{j,i} \tag{16}$$

Where j denotes the position on the segment.

For the purposes of calculating the contact forces, it will be assumed that all forces are acting in a single 2D plane. As such, it will also be assumed that all the net acting moments on the body are also only acting in this same 2D plane. For this reason, we need only concern ourselves with the magnitude of each of the moments which will be denoted as $m_j$ such that $\|m_j\|=m_j$. Also, it will be assumed that both moments at either end of the segment are equal in magnitude.

In order to determine when a contact has occurred, a model of the moment required to bend the segment 102 in a single 2D plane to a given angle θ must be found. This was based only on the tension measurements at the front end of the segment 102. This model, denoted $\theta \hat{m}_j(\theta)$, can be analytically derived or fitted to experimental data. In this case, experimental data was used to find that:

$$\hat{m}_{front}(\theta) \approx A \tan h(b\theta) \forall -\pi \leq \delta \leq \pi \tag{17}$$

where A and b are constants.

Before moving into the finite element model which allows the contact forces to be estimated, the boundary case where contact has just occurred must be considered.

In this model, it is assumed that the segment 102 is completely free before contact occurs and statically constrained after contact occurs. As such, the only moment relevant to the static case where contact occurs would be the net moment, that is, the applied moment from the actuators minus the reaction moment from the segment 102 itself. This net moment will be denoted $m_j^{net}$ and will be calculated using:

$$m_j^{net} = m_j - \hat{m}_j(\theta) \tag{28}$$

Finding this net moment is straight forward for the front end by using equations (16) and (17) to find $m_i$ and $\hat{m}_j(\theta)$ $m_j \cdot \hat{m}_j(\theta)$.

The contact forces before contact occurs are zero (by definition). It will be assumed that contact is occurring for all cases when the measured moment at the front end is greater than the predicted moment by some fixed amount γ such that $m_{front}^{net} > \gamma$. Here, γ is chosen based on experience to minimise false positive situations where the measured moment is slightly higher than the predicted moment due to hysteresis or any phenomena other than contact. When this condition is met, the contact angle θ* is recorded and used to derive the initial configuration of the segment in the static finite element model.

Once contact has occurred, it is assumed that the segment is in a static condition and all dynamic effects can be ignored. Hence, the static equilibrium conditions on forces and moments ($\Sigma f=0$ and $\Sigma m=0$) are assumed. Furthermore, all motions are assumed to be slow such that dynamic effects may be ignored.

Figure 19A:
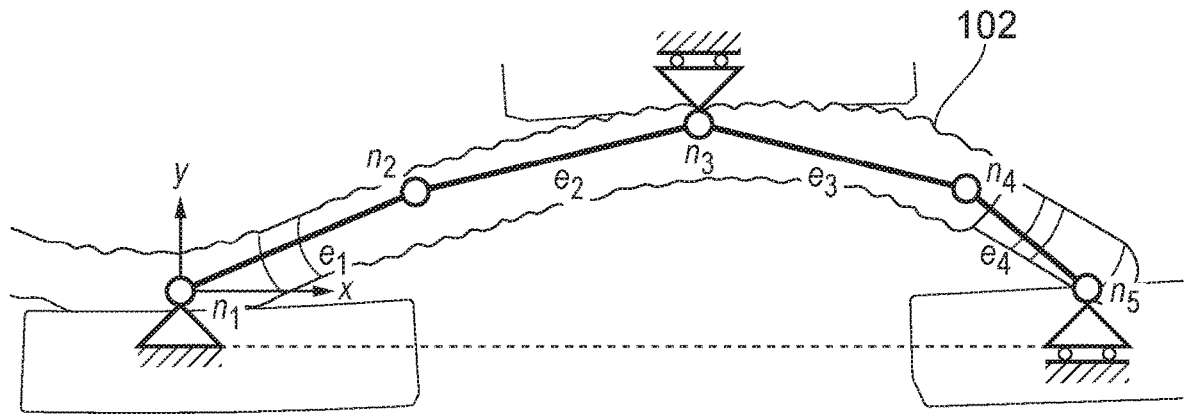
FIGS. 19a-c illustrate contact force and stiffness estimation using embodiments of the present invention.

The details and structure of the finite element model will depend on the application. Here, a simple example will be presented with the minimum number of elements. One segment will be modelled using 4 elements connected in series with 5 nodes in total. This model is shown in FIG. 19a, which shows the finite element mode overlaid on an image of a prototype segment performing anchoring. The nodes and elements are numbered sequentially from left to right and denoted with an n and e respectively. The two elements on either end are meant to represent rigid sections of the segment that house the actuating motors ($e_1$) and the camera and load cell housing ($e_4$). The elements $e_2$ and $e_3$ represent the soft body of the segment. Node 1 is assumed to be under a translational constraint but is able to rotate freely. Nodes 3 and 5 are constrained in the y direction but are otherwise free. All other nodes are free to translate or rotate.

In order to begin the finite element calculation, the position of each node must be established. Since the shape of the soft segment is available from the technique discussed above (or can be found using a more direct sensing approach such as fibre-Bragg-gratings or inertial sensing equipment), finding the node positions and orientations is a matter of simple geometry. The initial nodal positions are calculated using the contact angle $\theta^*$. As contact forces are very small at the initial moment of contact, it is assumed that the segment deformation due to these forces is minimal and the models described in above still hold. As will be shown later, at higher forces where the constant curvature model is invalid, the finite element model will be able to estimate the deformations that occur in each element (and therefore the compliant segment) from the nodal displacements.

Each node's position will be described using a vector $x_k=[x_k\ y_k\ a_k]^T$ where, k, indicates the node number, $x_k$ and $y_k$ are the planar coordinates according to the frame shown in FIG. 19a and $a_k$ is the rotation about the z-axis (pointing out of the page) relative to the x-axis. The $k^{th}$ node is experiencing two forces and one moment which will be written $p_k=[p_{k,x}\ p_{k,y}\ m_{k,z}]^T$. These include both reaction forces and applied forces.

Each element will have an associated stiffness matrix. This matrix is composed of values which are based on the physical properties of the materials used in each element and their geometry. In practice, it can be assumed that these properties are linear and constant (such as the cross-sectional area and the Young's modulus of the soft segment). This is a simplification, but has been found to be adequate for determining the contact forces. There are a number of stiffness matrices that have been proposed in the literature[33]. Here a simple 2D stiffness matrix for the $k^{th}$ element was used which ignores shear forces and is given by: $x_k=[x_k\ y_k\ \alpha_k]^T$ $$K'_k = \frac{E_k I_{k,z}}{l_k^3} \begin{bmatrix} \frac{A_k l_k^2}{I_{k,z}} & . & . & . & . & . \\ 0 & 12 & . & . & \text{symmetric} & . \\ 0 & 6l_k & 4l_k^2 & . & . & . \\ -\frac{A_k l_k^2}{I_{k,s}} & 0 & 0 & \frac{A_k l_k^2}{I_{k,s}} & . & . \\ 0 & -12 & -6l_k & 0 & 12 & . \\ 0 & 6l_k & 2l_k^2 & 0 & -6l_k & 4l_k^2 \end{bmatrix} \quad (19)$$

Figure 19B:
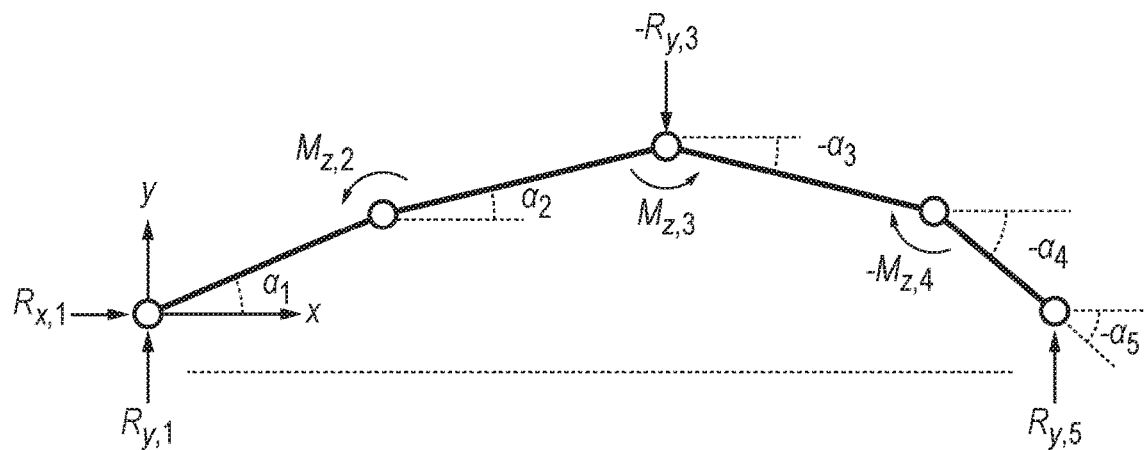

The finite element technique used here will rely on Hooke's law to solve for both the unknown displacements and the unknown forces. In matrix form, Hooke's law is written:

$$p^G = K^G \delta x^G \quad (20)$$

Where $p^G$ and $\delta x^G$ are the global force and change in displacement vectors respectively and $K^G$ is the global stiffness matrix. It must be noted that $\delta x^G$ consists of changes in nodal position relative to the initial contact state. Each stiffness matrix must be adjusted to account for the orientation of each element. This rotated matrix is calculated based on the angles found from the constant curvature model. This rotation is calculated as follows:

$$K_k = R^T(\alpha_k) K_k' R(\alpha_k) \quad (21)$$

Where $\alpha_k$ is the angle of the $k^{th}$ element with respect to the x-axis as shown in FIG. 19b, which shows an illustration of the coordinates and applied forces in the finite element model.

For more information on how $R(\alpha_k)$ is constructed, see reference 33 below.

The force and displacement vectors are assembled as follows:

$$p^G = [p_1 p_2 p_3 p_4 p_5]^T \quad (22)$$

$$\delta x^G = [\delta x_1 \delta x_2 \delta x_3 \delta x_4 \delta x_5]^T \quad (23)$$

Based on this organisation and the finite element structure in FIG. 19b, the global stiffness matrix will be a square matrix with 15 values on each side; there is one value for each element (4 in total); and is given by $$K^o = \begin{bmatrix} K_1 & \cdots & 0 \\ \vdots & 0 & \vdots \\ 0 & \cdots & 0 \end{bmatrix} + \begin{bmatrix} 0_{3\times 3} & 0 & 0 \\ 0 & K_2 & 0 \\ 0 & 0 & 0 \end{bmatrix} + \begin{bmatrix} 0_{6\times 6} & 0 & 0 \\ 0 & K_3 & 0 \\ 0 & 0 & 0 \end{bmatrix} + \begin{bmatrix} 0 & \cdots & 0 \\ \vdots & 0 & \vdots \\ 0 & \cdots & K_4 \end{bmatrix} \quad (24)$$

For more information on how to assemble stiffness matrices, please see reference 33.

Now, using equation 20, we can identify which variables are known and which are unknown. From the modelling and measurements described earlier, the known forces are the three moments acting at nodes 2, 3 and 4. These are defined as follows: $m_{2,z} = m_{rear}^{net}$, $m_{3,z} = m_{fric}$ and $m_{4,z} = m_{front}^{net}$. The unknown forces are the reaction or contact forces denoted as $R_{x1}$, $R_{y,1}$, $R_{y,3}$ and $R_{y5}$. All other forces are zero. Hence, there are 4 unknown force variables. Looking at the displacement vector, the constraints dictate that $\delta x_1$, $\delta y_1$, $\delta y_2$ and $\delta y_5$ all equal zero. Hence, the 11 other displacements are unknowns.

Putting this all together, we have a linear system of equations given by (20) where there are 15 equations (three degrees of freedom per node and 5 nodes) and 15 unknowns (4 unknown contact forces and 11 unknown displacements). In each degree of freedom, if the force is known, then the displacement is unknown and vice-versa. There is never a case where both a force and a displacement is unknown for a given degree of freedom. As a result, this system of linear equations is fully constrained and can be solved by using any number of methods such as the matrix displacement method or the matrix force method[33]. Thus, the unknown displacements and forces may be calculated.

Figure 20A:
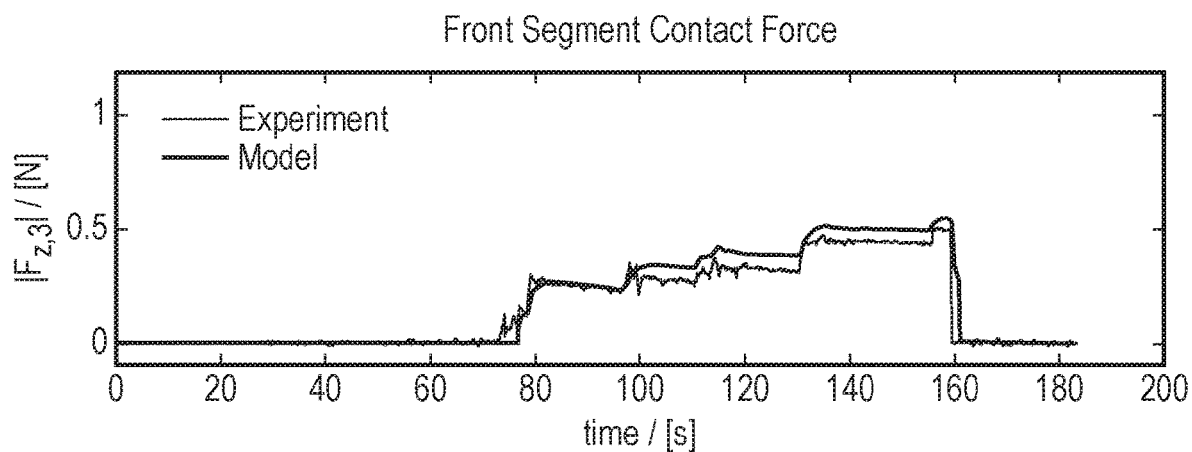
FIGS. 20a-c are graphs illustrating contact force estimation using embodiments of the present invention.
Figure 20B:
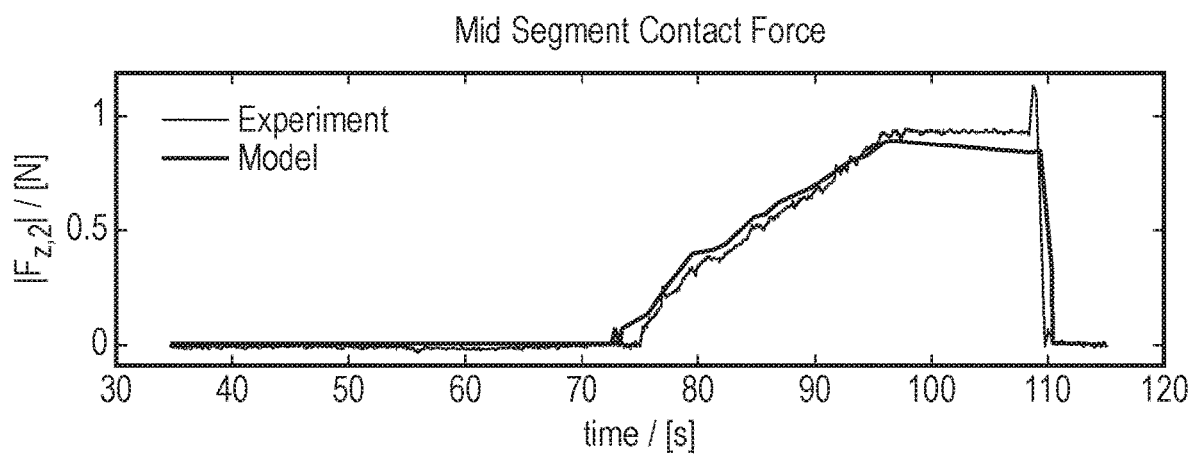
Figure 20C:
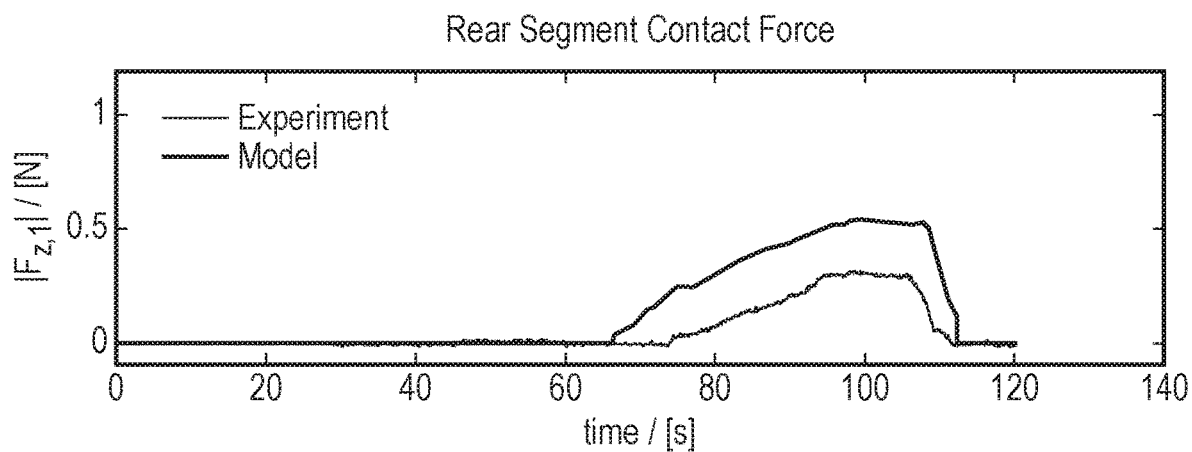

An example of the results achievable from this method are given in FIGS. 20a-c, which show experimental measurements and modelled prediction of the contact forces exerted by the segment on a compliant surface during anchoring and the error in the force prediction compared to the measured forces.

In general, there is good agreement with the true force as measured by a high accuracy load cell. Contact detection is not always perfect, but can possibly be improved by implementing a more complex contact detection system. The accuracy is generally better than +/−0.2 N which could be improved by more detailed modelling that takes into account the non-linearity of the structure. The limitations of this method are that it assumes that the environment is much stiffer than the structure of the segment itself and therefore has minimal deformation as a result of the segment pressing against it (hence why the constraints assume zero displacement in some directions). This, however, can be accounted for provided sufficient shape sensing equipment is available. This is discussed below.

Stiffness Estimation

The method of contact force estimation described above can be extended to account for compliance in the constraints that were previously assumed to be completely rigid. This would require that the shape of the segment is sensed more accurately, rather than basing it purely on the tendon lengths. As an upshot, this would also allow the segment to measure the stiffness of the compliant environment.

The additional sensing required could be achieved by using a number of accepted methods for shape detection in continuum robotic segments. These include use of inertial measurement units (IMUs), magnetic fields, Fibre-Bragg-Gratings and many others[34]. Many of these methods rely on sensing relative orientation of several points along the body of a single segment. Assuming a constant curvature between each of these points—while still a simplification—would increase the accuracy of the shape sensing proportionally to the number of sensing points.

If it is assumed that the segment is equipped with a sufficient number of sensors to provide accurate shape feedback while the segment is in contact with a compliant environment, then this information can be fed into equation 20 to solve for the stiffness of the environment.

Figure 19C:
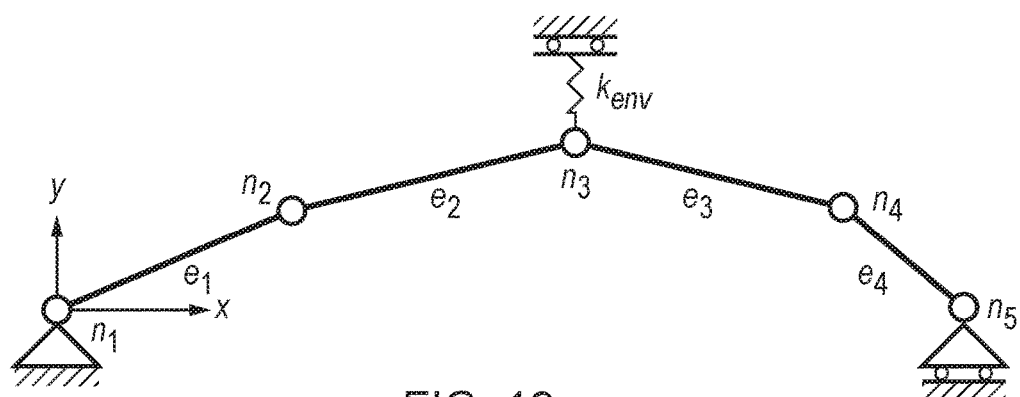

The simplest implementation of this would use an adapted finite element model as shown in FIG. 19c, which shows a modified version of the finite element model that accounts for compliance in the environment. Here, it is assumed that only stiffness in the y-direction (denoted $k_{env}$) is of interest. To compute this stiffness, the same procedure as that outlined in the previous section is followed until the final step where equation 20 is solved. Here, rather than assuming that $\delta y_3 = 0$, it will be taken from the enhanced shape sensor readings. All other nodal displacements may also be taken from these sensor readings if needed. The displacement referred to hear would only be the displacement after contact has occurred. Detecting the moment of contact could be performed similarly to the technique suggested previously.

With these nodal displacements, equation 20 is solved to find $p^G$. Once done, the stiffness of the environment may be derived from the scalar version of Hooke's law or any other desired stiffness model. For linear material obeying Hooke's law, the stiffness of the environment would be given by:

$$k_{env} = \frac{\delta y_3}{R_{y,3}} \quad (25)$$

Hence, the stiffness of the environment (in at least one direction) can be estimated. In applications such as endoscopy, the ability to measure stiffness of the environment in which the device is deployed can be useful for diagnosis purposes. For example, measuring the stiffness of the colon can be used to detect scarring on the wall of the colon, which itself can be indicative of an underlying medical issue such as Irritable Bowel Syndrome or Crohn's disease.

Hydraulic Configuration

A hydraulically or pneumatically actuated device will now be described in more detail.

Segment Design

In an effort to both simplify and miniaturize the construction of a segment, a robotic device comprising a plurality of fluid actuated segments has been designed. A segment 2100 for use in such as device is shown in FIGS. 21a-b and 22a-b. The segment 2100 consists of a core 2102, made of a soft, flexible material such as rubber, along with an external reinforcement means 2108 and several internal reinforcement means 2104, such as a spring, a coil, a series of hoop structures or a wound up thread of resilient material such as a wire, to constrain the core 2102 while under deformation. In FIGS. 21a-b and 22a-b, the internal reinforcement means 2104 and external reinforcement means 2108 are in the form of a cylindrical bellows structure, similar to that of a concertina. The internal reinforcement means 2104 and external reinforcement means 2108 may be made of any suitable material such as metal.

A plurality of actuation chambers 2106 are provided in the form of cavities inside of the core 2102. In use, these cavities 2106 are filled with a fluid such as air or water and sealed to prevent the fluid from escaping. An external pump (not shown) is used to either increase or decrease the volume of fluid inside of each cavity 2106 via a small tube and thus enables actuation of each segment 2100. The pump will be described in more detail below. How the actuation alters the shape of the segment 2100 will depend on the spatial arrangement of these actuation chambers 2106 inside of the core 2102.

The soft rubber core 2102 will tend to "balloon" when the actuation chambers 2106 are inflated with fluid. This produces undesirable deformation which is both hard to predict and not useful for producing the pure bending needed for the invention. In order to prevent this, the external reinforcement means 2108 placed around the outside of the core 2102 is stiffer in the radial direction and relatively less stiff when bending or extending. In this respect, the external reinforcement means 2108 may be of any suitable configuration, for example, in the form of a spring, a coil, a wound up thread of resilient material, or a concertina-like structure. As the external reinforcement means 2108 is significantly stiffer in the radial direction, the core 2102 is prevented from ballooning. Since the external reinforcement means 2108 is significantly less stiff when bending or extending, pumping fluid into a single actuation chamber 2106 has the effect of causing that particular actuation chamber 2106 to only elongate, thus causing the segment 2100 to expand in the longitudinal direction. Conversely, pumping fluid back out of an actuation chamber 2106 has the effect of causing that particular actuation chamber 2106 to shorten, thus causing the segment 2100 to contract in the longitudinal direction. In order to make a segment 2100 bend, the amount of fluid pumped in or out of the actuation chambers 2106 is varied to achieve varying levels of expanding or contracting. For example, to bend a segment 2100, fluid will be pumped in to an actuation chamber 2106 at one radial position causing expansion in the longitudinal direction, whilst fluid is pumped out of an actuation chamber 2106 at the opposite radial position causing contraction in the longitudinal direction. As such, each actuation chamber 2106 is controlled in a similar way to the tendons 402 in the embodiment described above.

In addition to the outer reinforcement means 2108, any number of internal reinforcement means 2104 can be placed inside of the core 2102, allowing the creation of conduits 2110 that will bend and extend with the rest of the segment 2100 when under actuation. Again, an increased radial stiffness of the internal reinforcement means 2104 constrains the lateral expansion of the actuation chambers 2106 and prevents the conduits 2110 and/or other actuation chambers 2106 from closing as fluid is pumped into the actuation chambers 2106. This helps to improve the overall performance and accuracy of the device by reducing hysteresis, that is, by increasing the response of each segment 2100 to fluid being pumped in and out of the actuation chambers 2106, and by reducing cross-coupling, that is, limiting the effect that the actuation of one actuation chamber 2106 has on other actuation chambers 2106 within the same segment 2100.

The bending and extending properties of the internal reinforcement means 2104, however, allow each conduit 2110 to deform with the core 2102 while allowing the free passage of any tubes, wires or instruments through each conduit 2110, as will be discussed in more detail below.

The contracting properties of both the external reinforcement means 2108 and the internal reinforcement means 2104 also helps the segments 2100 to return to their original configuration. That is to say, when fluid is not being pumped in or out of the actuation chambers 2108, the external reinforcement means 2108 and the internal reinforcement means 2104 are configured to bias the segments 2100 into a straight position.

It will be appreciated that the external reinforcement means 2108 and the internal reinforcement means 2104 may comprise any suitable means that has a radial stiffness capable of constraining any lateral of the actuation chambers 2106, and otherwise capable of contracting and extending along the longitudinal axis, and bending at an angle to the longitudinal axis. For example, the external reinforcement means 2108 and/or internal reinforcement means 2104 may comprise a series of metal hoops, a wound thread of resilient material, or a concertina-like structure, as shown in FIGS. 21*a-b* and 22*a-b*. An external reinforcement means 2108 and internal reinforcement means 2104 in the form of a spring is particularly advantageous since it inherently has the properties required. That is to say, a spring is configured to extend and contract along its longitudinal axis, and bend at an angle to the longitudinal axis, whilst being radially stiff enough to constrain any lateral expansion of the actuation chambers 2106.

As with the previous embodiment, a number of segments 2102, for example, three segments 2102, may be coupled together to form a device such as an endoscope, the segments 2102 being enclosed in a protective sheath 2112 made of any suitable material, for example, latex. Further details of materials that may be used to encase the segments 2102 will be described below.

Segment Manufacture

One example of a method of manufacturing a segment 2102 for use in a fluid actuated device will now be described. To manufacture a fluid actuated segment 2102, the inner and outer reinforcement means 2104, 2108 are arranged in the desired configuration inside of a mould. The mould is then filled with a rubber-like compound that is liquid in its uncured state.

Once cured, this compound forms the soft core 2102. A similar (ideally stiffer) rubber-like compound is then poured over the open ends of the core so as to plug the actuation chambers 2106 forming caps or plugs in order to seal them, while ensuring that each chamber still encloses sufficient empty space in which fluid may be pumped. In practice, it is crucial that the compound used for the caps will bond to the cured rubber core 2102 in order to create a strong seal when under pressure, but any similar method that will result in the sealing of the actuation chambers (such as using adhesive to fix a plug over an actuation chamber's opening) will suffice.

Once the caps are cured, tubes may be inserted through the caps into each actuation chamber 2106 to allow actuation. These tubes may be glued to the cap material or allowed to bond with the cap material during curing if the tube material is capable of this.

In practice, silicone rubber has been used to create the rubber core 2102. A significantly stiffer silicone rubber is then used for the caps. The tubes are made from PTFE (Polytetrafluoroethylene) and are glued using a Cyanoacrylate (super glue) after chemically etching the outer surface of the tubes. Varying the stiffness of the silicone rubber core 2102, the diameter and materials of the wires used in the reinforcement means will enable each individual segment's stiffness to be tuned according to the requirements of any particular design.

This manufacturing technique would allow rapid and low cost production of segments 2100 in large volumes. This is because the individual component parts (rubber core, rubber cap and reinforcement means) are relatively low cost and each mould can be reused once the core has cured. Also, from a labour point of view, each mould could potentially be prepared by a machine, thus further reducing the manufacturing cost.

With regard to the size of the segment, the current prototype is about 16 mm in diameter. This, however, can be significantly reduced by use of specially manufactured reinforcement means and reducing the size of the conduits 2110.

Pump Design

Figure 23:
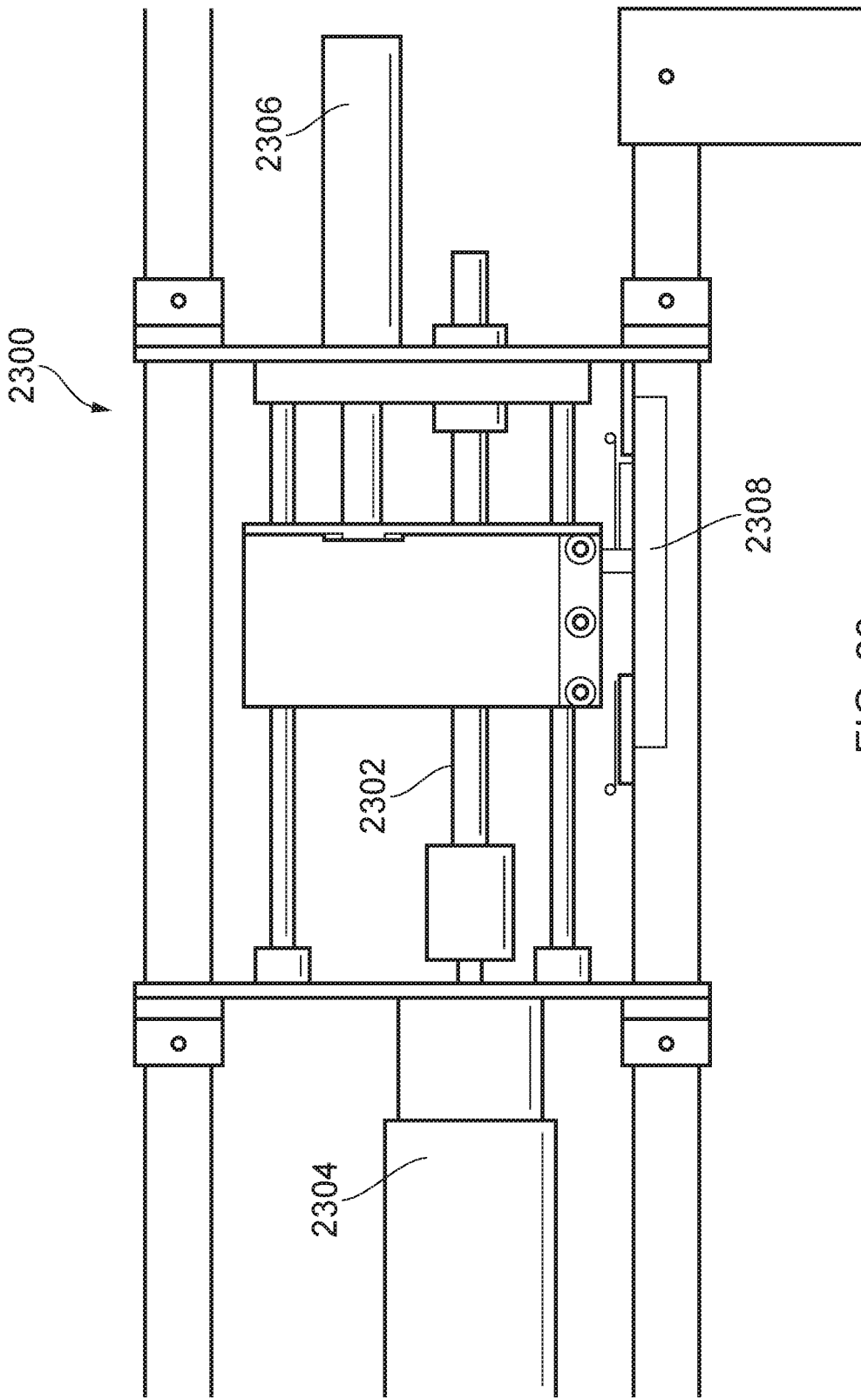
FIG. 23 illustrates a pump used to drive a device according to an embodiment of the present invention.

A pump used to actuate the actuation chambers 2106 of each segment 2100 will now be described with reference to FIG. 23. FIG. 23 shows a single syringe pump 2300 used to actuate a single actuation chamber 2106, as described above.

The pump 2300 comprises a leadscrew 2302 used to convert the rotation of an electric motor 2304 into a linear motion which can push and pull the plunger (not shown) on a syringe 2306. By using an incompressible fluid such as water to actuate the chamber 2106, the volume of liquid inside of each chamber 2106 can be estimated from the distance traveled by the syringe plunger. Here, a linear potentiometer 2308 is affixed to the platform which drives the syringe plunger and thus allows estimation of the volume pumped into the actuation chamber 2106.

In addition to volumetric feedback, pressure sensors (not shown) can be mounted to the tubing connecting each pump with each actuation chamber, allowing the pressure inside of each actuation chamber 2106 to also be measured.

Knowledge of the internal pressure and the volume of each actuation chamber 2106 serves a similar function to tension and tendon length respectively in the motorised embodiment of the segments 102, 104, 106 described above. Thus, a similar approach can be used to estimate the contact forces produced by a single segment 2100, and subsequently measure the stiffness of the walls of the environment in which the device is deployed, as described above.

On-Board Biopsy Tool

Figure 22B:
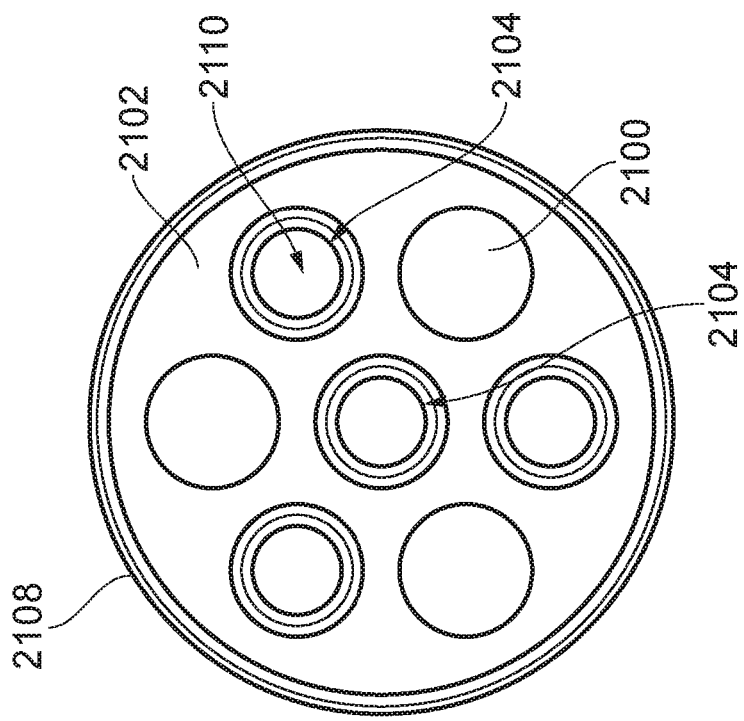
FIG. 22a is a perspective view of part of a device according to an embodiment of the present invention.
FIG. 22c is a cross-sectional view of part of a device according to an embodiment of the present invention.
Figure 22A:
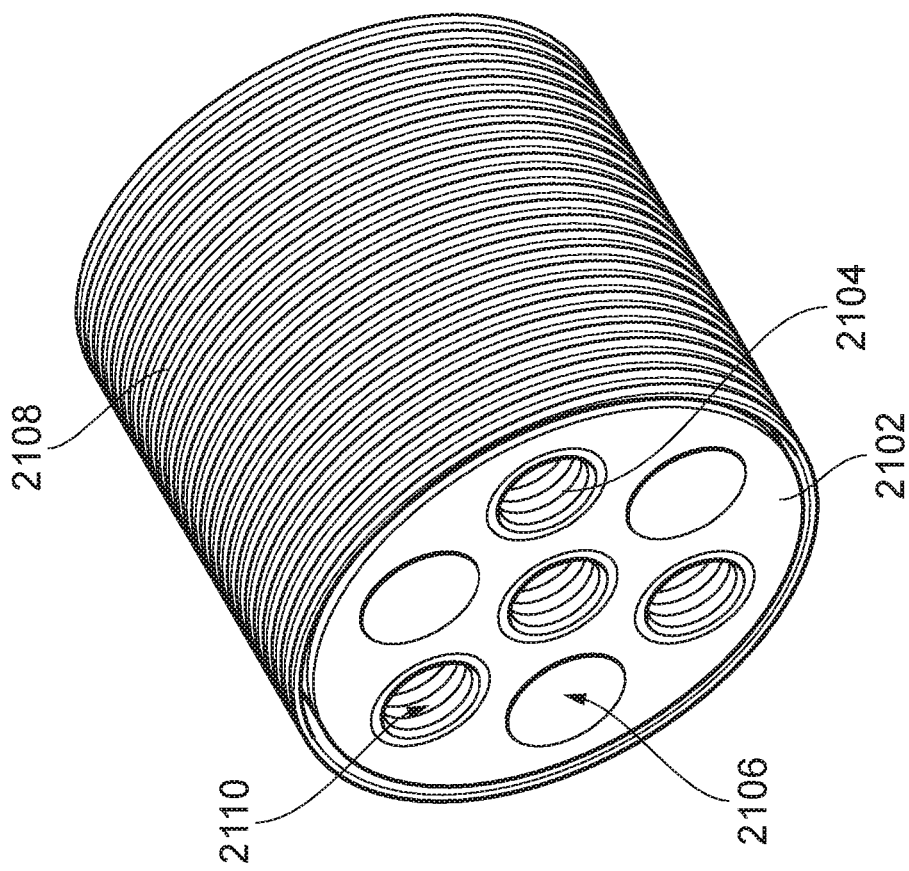

The reinforced conduits 2110 of the fluid actuated segments 2100 shown in FIGS. 21 and 22a-b are configured so as to accommodate standard biopsy tools used in endoscopy, as will now be described with reference to FIGS. 24a-c.

Figure 24A:
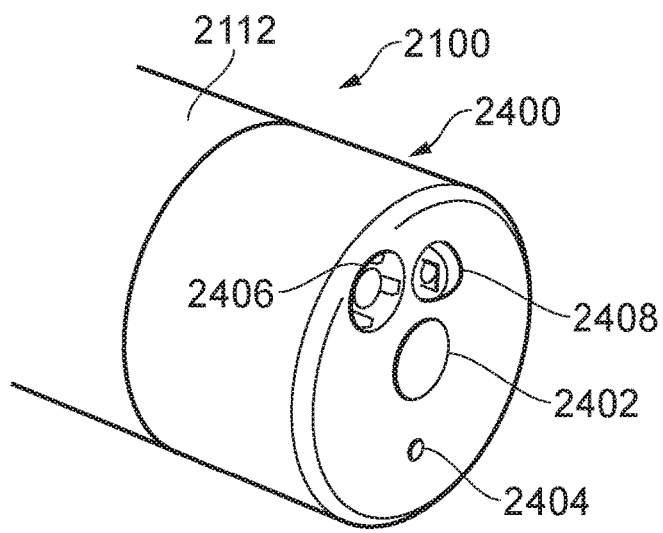
FIG. 24a is a perspective view of part of a device according to an embodiment of the present invention.
Figure 24B:
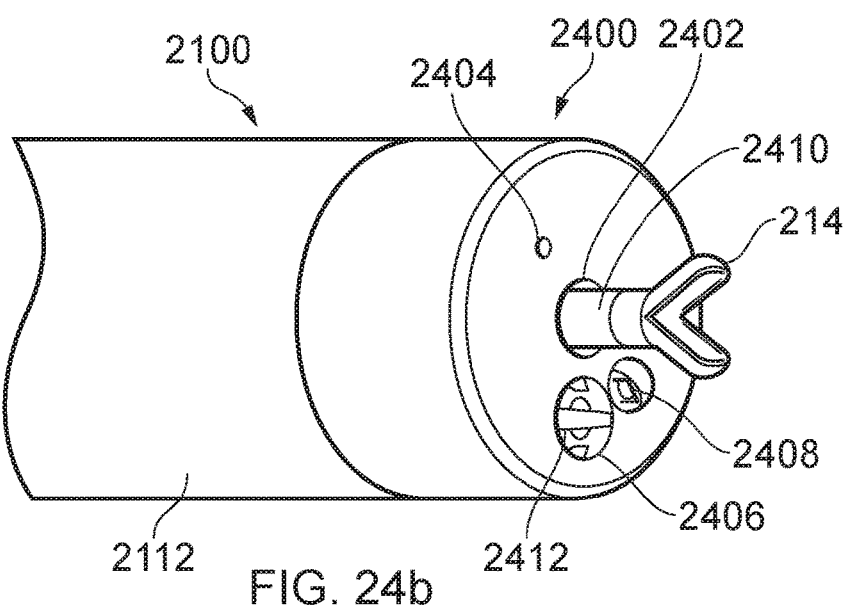
FIG. 24b is a perspective view of part of a device according to an embodiment of the present invention.
Figure 24C:
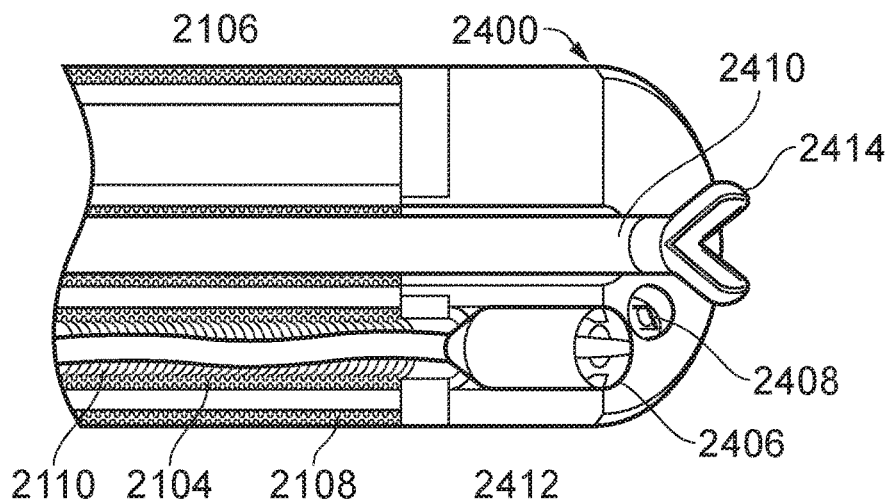
FIG. 24c is a cross-sectional view of part of a device according to an embodiment of the present invention.

FIGS. 24a-c show the distal end of an end segment 2100, for example, the leading segment 2100 when used for endoscopic purposes. The end of the segment 2100 is provided with a cap 2400 having a number of outlets, including but not limited to, an instrument outlet 2402, a first fluid outlet 2404, an imaging outlet 2406 and a second fluid outlet 2408. The instrument outlet 2402 is configured to allow a biopsy tool 2410 to extend out of the distal end of the segment 2100. Any suitable biopsy tool 2410 may be passed through the segment 2100, for example, the biopsy tool 2410 may comprise an end effector in the form of a pair of jaws 2414, as shown in FIG. 24b. These jaws 2414 may include electrodes such that the jaws 2414 are configured to cut and coagulate tissue. The instrument outlet 2402 may also be configured to output fluid, pump in fluid and create suction. The imaging outlet 2406 is configured to retain a camera and light arrangement 2412, the second fluid outlet 2408 being configured to output fluid for cleaning the lens of the camera/light arrangement 2412.

As can be seen from FIG. 24c, the cables connected to the biopsy tool 2410 and camera/light arrangement 2412 extend through the conduits 2110 formed by the internal reinforcement means 2104. The standard diameter of the conduits 2110 is around 2.8 mm. Therefore, an internal reinforcement means 2104 such as a spring or wound up thread of resilient material with an inner diameter equal to or greater than this may be embedded in the core 2102 to allow such a biopsy tool 2410 to be passed from the outside to the distal end of the segment 2100, which may be via a series of further segments 2100, as will now be discussed.

Figure 25:
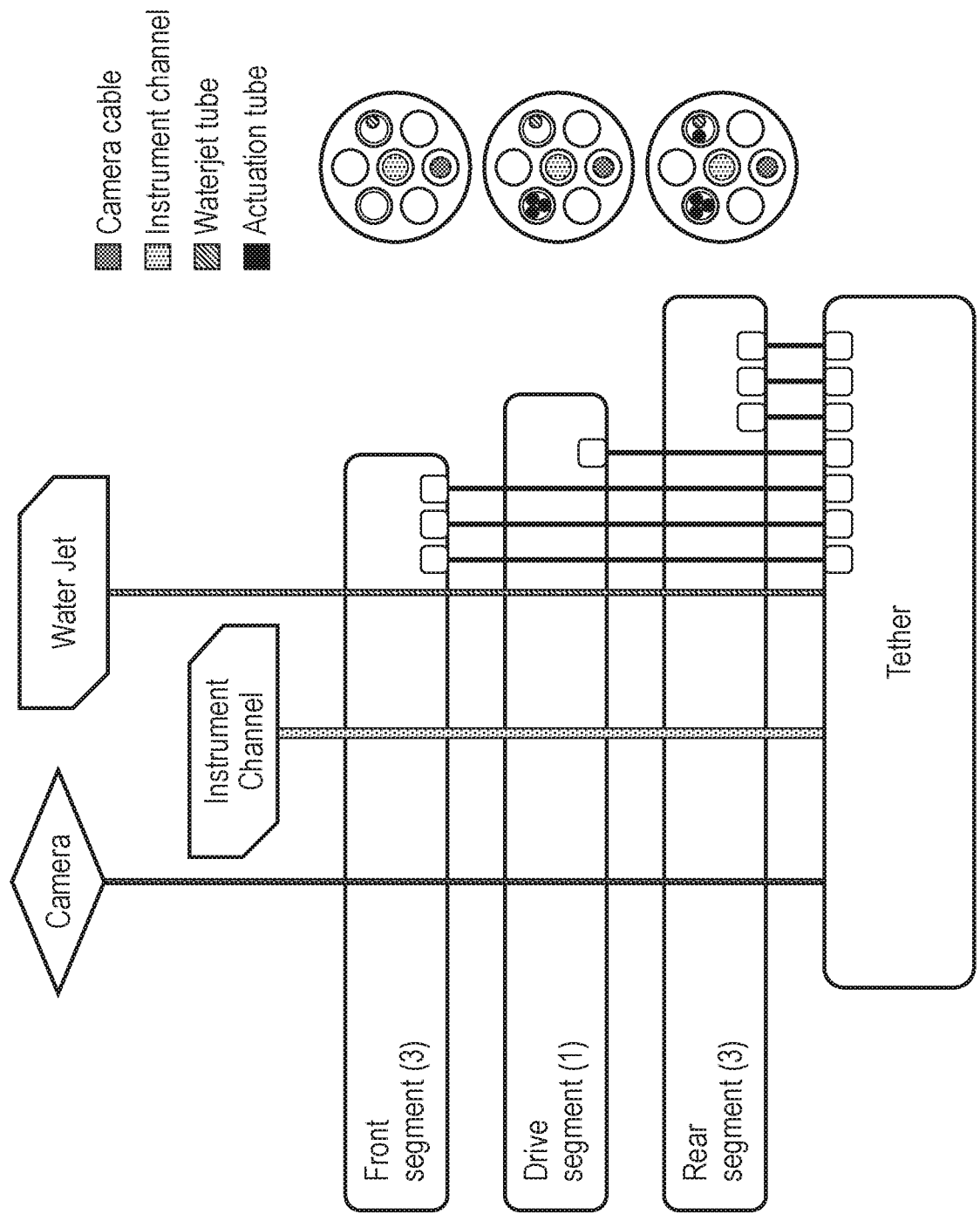
FIG. 25 is a block diagram illustrating the configuration of a device according to an embodiment of the present invention.

FIG. 25 provides an example of how a 3-segment device using the same configuration as the motorized tendon embodiment of the robotic device described with reference to FIG. 2 would use conduits 2110 to pass tubes, cables and instruments from the various segments to the attached tether.

These conduits 2110 also allow tubing and wires to be passed from one segment to either the outside, or another segment. For example, a configuration similar to that of FIG. 2 uses three segments and has 7 degrees of freedom. As described above, it may be necessary to provide biopsy tools 2410 passing through the instrument channel 2402, a tube connecting an external pump to the first fluid outlet 2404 to produce a water jet and finally, an electrical cable passing from the camera/light arrangement 2412 situated at the distal end to a computer outside of the device. As such, 7 actuation tubes, 1 water jet tube, 1 cable and 1 instrument channel may pass through these three segments to a tether. This tether is then coupled to an actuation and processing unit, which houses the pump actuators and an image visualisation system.

Skin Friction Mechanism

Figure 26:
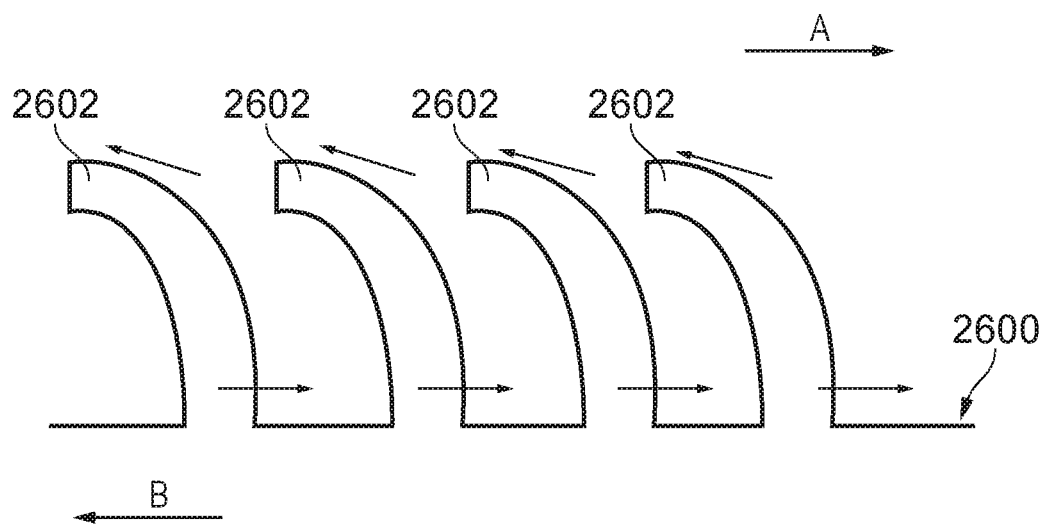
FIG. 26 illustrates a first surface of a device according to an embodiment of the present invention.

The implementation of the above noted skin friction mechanism will now be described in more detail. The material used to encase the device may be adapted so as to control the frictional interaction between the segments 102, 104, 106, 2100 and the surface of the environment in which the device is deployed. One example of a material is provided in FIG. 26, which illustrates the configuration of the surface 2600 of said material. The surface 2600 has a hook-like or "cilia" configuration comprising rows of backwards facing fibre-like hooks 2602. When the device moves forwards along a cavity such as a colon, in the direction of arrow A, the hooks 2602 lie flat in the opposite direction to allow the device to move through the cavity without resistance. If the device slips back along the cavity, in the direction of arrow B, the hooks 2602 move in the opposite direction such that they stand up, such that they grip against the walls of the cavity and thereby prevent the device from slipping backwards. However, it will be appreciated that when the device is to be actuated in the opposite direction, that is, to exit the cavity, the force of the actuation is sufficient to overcome the resistance provided by the hooks 2602.

Alternatively, the material used to encase the device may comprise a "fish scale" arrangement, comprising a plurality of small disk or plate like structures or "scales" configured to work in a similar way as the hook arrangement, whereby the scales flatten as the device moves forward, and fan outwards if the device slips back.

Figure 27A:
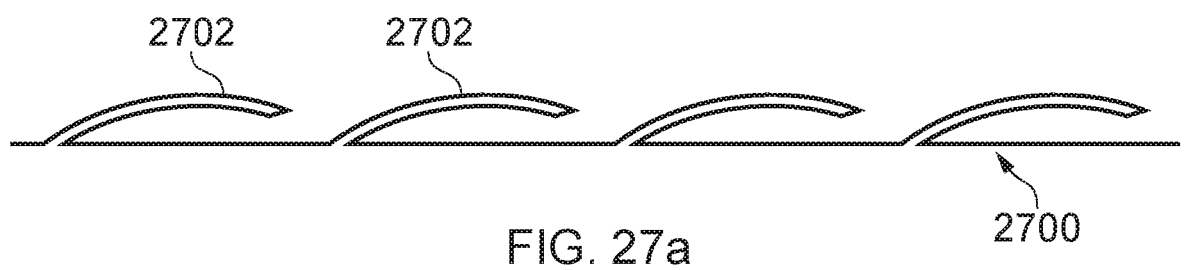
FIGS. 27a-b illustrate a second surface of a device according to an embodiment of the present invention.
Figure 27B:
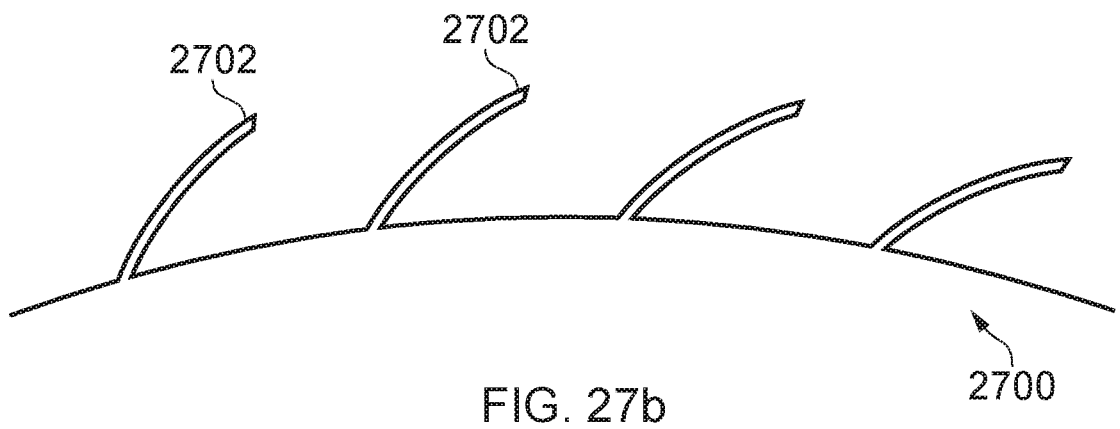

The effect of such materials as a device bends is demonstrated by FIGS. 27a-b and 28a-b. FIG. 27a shows a surface 2700 having a plurality of single direction scales or fibres 2702, the surface 2700 being in a straight position. Here, the fibres 2702 are lying substantially flat against the surface 2700. FIG. 27b illustrates the surface 2700 as the segment which it is covering bends. Here, the fibres 2702 have unfolded such that they stand up, substantially perpendicular to the surface 2700, to thereby enhance the locomotive movement of the device in a particular direction.

Figure 28A:
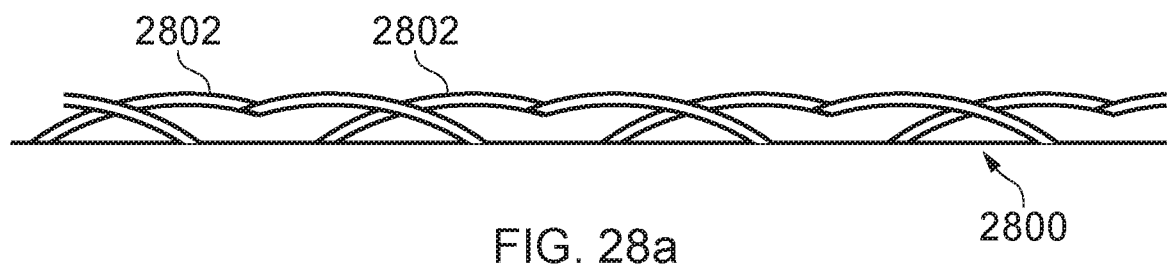
FIGS. 28a-b illustrate a third surface of a device according to an embodiment of the present invention.
Figure 28B:
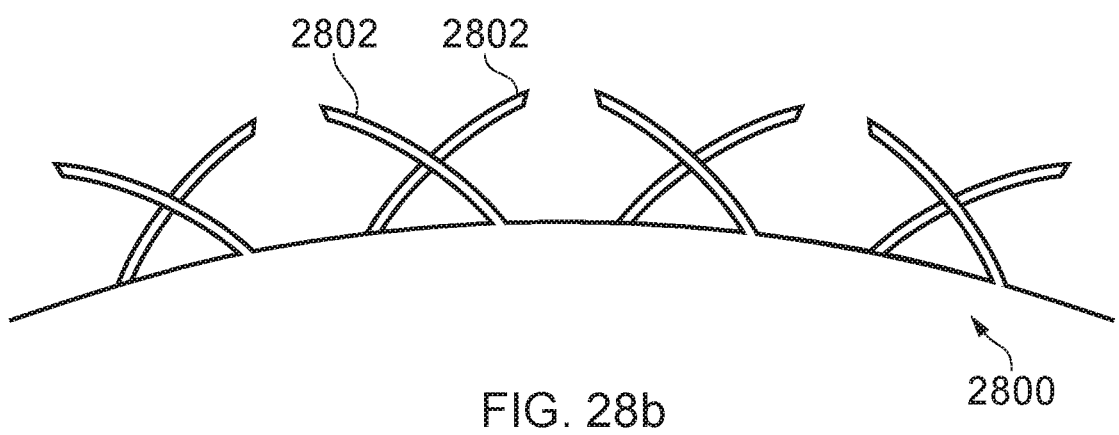

FIG. 28a shows a surface 2800 having a plurality of multi-direction scales or fibres 2802, the surface 2800 being in a straight position. Here, the fibres 2802 are lying substantially flat against the surface 2800. FIG. 28b illustrates the surface 2800 as the segment which it is covering bends. Here, the fibres 2802 have unfolded such that they stand up, substantially perpendicular to the surface 2800, to thereby prevent sliding in both directions for effective anchoring.

By encasing the device in materials having the above configurations, this improves the device's ability to move around corners of up to around 180°. As such, the combined effect of the locomotive motion, the anchoring of the segments between the walls of its environment and the hooking or anchoring action by the outer surface of the device makes it easier for the device to hook and pull itself around corners and bends.

The above surfaces may be made of any suitable material, for example, urethane rubber PMC-780.

Various modifications, whether by way of addition, deletion and/or substitution, may be made to all of the above described embodiments to provide further embodiments, any and/or all of which are intended to be encompassed by the appended claims.

[1] Loeve, a. J., "Shaft-Guidance for Flexible Endoscopes," Ph.d. thesis. Dept. BioMechanical Engineering, Delft Univ of Technology, Delft, Netherlands, 2012.

[2] F. Stracci, M. Zorzi, and G. Grazzini, "Colorectal Cancer Screening: Tests, Strategies, and Perspectives," Frontiers in Public Health, vol. 2, no. October, pp. 1-9, 2014.

[3] A. Loeve, P. Breedveld, and J. Dankelman, "Scopes Too Flexible . . . and Too Stiff," IEEE Pulse, vol. 1, no. 3, pp. 26-41, 2010.

[4] A. May, L. Nachbar, and C. Ell, "Double-balloon enteroscopy (push-and-pull enteroscopy) of the small bowel: Feasibility and diagnostic and therapeutic yield in patients with suspected small bowel disease," Gastrointest. Endosc., vol. 62, no. 1, pp. 62-70, 2005

[5] H. Yamamoto, Y. Sekine, Y. Sato, T. Higashizawa, T. Miyata, S. Iino, K. Ido, and K. Sugano. "Total enteroscopy with a nonsurgical steerable double-balloon method." Gastrointestinal endoscopy, San Diego, Calif., MA, Rep. May. 2000

[6] M. R. Yuce and T. Dissanayake "Easy-to-swallow wireless telemetry", IEEE Microw. Mag., vol. 13, no. 6, pp. 90-101 2012

[7] G. Iddan, G. Meron, A. Glukhovsky, and P. Swain, "Wireless capsule endoscopy," Nature, vol. 405, no. 6785, p. 417, 2000.

[8] P. Dario, M. C. Carrozza, and A. Pietrabissa, "Development and in vitro testing of a miniature robotic system for computerassisted colonoscopy," Comput. Aided Surg., vol. 4, no. 1, pp. 1-14, 1999.

[9] H. D. Hoeg, A. B. Slatkin, J. W. Burdick, and W. S. Grundfest, "Biome-chanical modeling of the small intestine as required for the design and operation of a robotic endoscope," in Proc. 2000 IEEE Int. Conf. Robot. Automat., San Francisco, Calif., April 2000, pp. 1599-1606.

[10] P. Dario, M. C. Carrozza, L. Lencioni, B. Magnani, and S. D'Attanasio. "A microrobotic system for colonoscopy." In Robotics and Automation, 1997. Proceedings, 1997 IEEE International Conference on, vol. 2, pp. 1567-1572. IEEE, 1997.

[11] S. Kumar, I. M. Kassim and V. K. Asari "Design of a vision-guided microrobotic colonoscopy system", Adv. Robot, vol. 14, pp. 87-104 2000

[12] K. Wang, G. Yan, P. Jiang, and D. Ye, "A wireless robotic endoscope for gastrointestine," IEEE Transactions on Robotics, vol. 24, no. 1, pp. 206-210, 2008.

[13] W. Lin, Y. Shi, Z. Jia, and G. Yan, "Design of a wireless anchoring and extending micro robot system for gastrointestinal tract," The International Journal of Medical Robotics and Computer Assisted Surgery: MRCAS, vol. 9, pp. 167-179, 2013.

[14] E. V. Mangan, D. A. Kingsley, R. D. Quinn, and H. J. Chiel, "Development of a Peristaltic Endoscope," in Proceedings of the 2002 IEEE International Conference on Robotics & Automation, 2002, no. May, pp. 347-352.

[15] A. Menciassi, S. Gorini, G. Pernorio, and P. Dario, "A SMA actuated artificial earthworm," IEEE International Conference on Robotics and Automation, 2004. Proceedings, vol. 4, pp. 3282-3287, 2004.

[16] A. Menciassi, D. Accoto, S. Gorini, and P. Dario, "Development of a biomimetic miniature robotic crawler," Autonomous Robots, vol. 21, no. 2, pp. 155-163, 2006.

[17] S. Seok, C. D. Onal, K. J. Cho, R. J. Wood, D. Rus, and S. Kim, "Meshworm: A Peristaltic Soft Robot with Antagonistic Nickel Titanium Coil Actuators," IEEE/ASME Transactions on Mechatronics, vol. 18, no. 5, pp. 1485-1497, 2013.

[18] K. Ikuta, M. Tsukamoto, and S. Hirose, R. H. Taylor, S. Lavallee, G. Burdea, and R. Mosges, "Shape memory alloy servo actuator system with electric resistance feedback and application for active endoscope", Computer-Integrated Surgery, pp. 277-282 1996:MIT Press

[19] P. Valdastri, M. Simi, and R. J. Webster, "Advanced Technologies for Gastrointestinal Endoscopy," Annual Review of Biomedical Engineering, vol. 14, no. 1, pp. 397-429, 2012.

[20] J. Pfeffer, R. Grinshpon, D. Rex, B. Levin, T. Rösch, N. Arber, and Z. Halpern, "The Aer-O-Scope: Proof of the Concept of a Pneumatic, Skill-Independent, Self-Propelling, Self-Navigating Colonoscope in a Pig Model," Endoscopy, vol. 38, no. 2, pp. 144-148, 2006.

[21] T. Rösch, A. Adler, H. Pohl, E. Wettschureck, M. Koch, B. Wiedenmann, and N. Hoepffner, "A motor-driven single-use colonoscope controlled with a hand-held device: a feasibility study in volunteers," Gastrointestinal Endoscopy, vol. 67, no. 7, pp. 1139-1146, 2008.

[22] S. Groth, D. K. Rex, T. Rösch, and N. Hoepffner, "High Cecal Intubation Rates with a New Computer-Assisted Colonoscope: a Feasibility Study," The American Journal of Gastroenterology, vol. 106, no. 6, pp. 1075-1080, 2011.

[23] A. Eickhoff, R. Jakobs, A. Kamal, S. Mermash, J. F. Riemann, and J. van Dam, "In vitro evaluation of forces exerted by a new computer-assisted colonoscope (the NeoGuide Endoscopy System)," Endoscopy, vol. 38, no. 12, pp. 1224-1229, 2006.

[24] A. Eickhoff, J. Van Dam, R. Jakobs, V. Kudis, D. Hartmann, U. Damian, U. Weickert, D. Schilling, and J. F. Riemann, "Computer-Assisted Colonoscopy (The NeoGuide Endoscopy System): Results of the First Human Clinical Trial ('PACE Study')," American Journal of Gastroenterology, vol. 102, no. 2, pp. 261-266, 2007.

[25] F. Cosentino, E. Tumino, G. R. Passoni, E. Morandi, A. Capria "Functional evaluation of the Endotics System, a new disposable self-propelled robotic colonoscope: in vitro tests and clinical trial" International Journal of Artificial Organs, vol. 32, no. 8, pp. 517-527, 2009.

[26] T. Manwell, T. Vitek, T. Ranzani, A. Menciassi, K. Althoefer, and H. Liu, "Elastic Mesh Braided Worm Robot for Locomotive Endoscopy," in Engineering in Medicine and Biology Society (EMBC), 2014 36th Annual International Conference of the IEEE, pp. 848-851, 2014.

[27] A. Alazmani, A. Hood, D. Jayne, A. Neville, and P. Culmer, "Quantitative assessment of colorectal morphology: Implications for robotic colonoscopy," Medical Engineering and Physics, vol. 38, no. 2, pp. 148-154, 2016.

[28] P. B. Cotton, P. Connor, D. McGee, P. Jowell, N. Nickl, S. Schutz, J. Leung, J. Lee, and E. Libby, "Colonoscopy: practice variation among 69 hospital-based endoscopists," Gastrointestinal Endoscopy, vol. 57, no. 3, pp. 352-357, 2003.

[29] C. Stefanini, A. Menciassi, P. Dario, "Modeling and Experiments on a Legged Microrobot Locomoting in a Tubular, Compliant and Slippery Environment," The International Journal of Robotics Research, vol. 25, no. 5-6, pp. 551-560, 2006.

[30] I. D. Walker, "Continuous Backbone '"Continuum"' Robot Manipulators," Internation Scholarly research Notices: Robotics, vol. 2013, 2013.

[31] B. A. Jones and I. D. Walker, "Kinematics for multisection continuum robots," IEEE Transactions on Robotics, vol. 22, no. 1, pp. 43-55, 2006.

[32] M. Rolf and J. J. Steil, "Constant curvature continuum kinematics as fast approximate model for the Bionic Handling Assistant," IEEE International Conference on Intelligent Robots and Systems, pp. 3440-3446, 2012.

[33] J. S. Przemieniecki, Theory of Matrix Structural Analysis. New York: McGraw-Hill, 1968.

[34] P. Polygerinos, N. Correll, S. A. Morin, B. Mosadegh, C. D. Onal, K. Petersen, M. Cianchetti, M. T. Tolley, and R. F. Shepherd, "Soft Robotics: Review of Fluid-Driven Intrinsically Soft Devices; Manufacturing, Sensing, Control, and Applications in Human-Robot Interaction," Advanced Engineering Materials, vol. 19, no. 12, 2017.

The invention claimed is:

1. A locomotive device, the device having an elongate body comprising a plurality of segments, wherein a segment comprises:

a flexible body;

a plurality of actuation chambers each extending along the length of the flexible body, wherein the plurality of actuation chambers are configured to be actuated by means of a fluid to thereby cause the flexible body to contract and extend along the longitudinal axis of the device and/or bend at an angle to the longitudinal axis of the device; and a plurality of conduits each extending along the length of the flexible body, wherein the plurality of actuation chambers and the plurality of conduits are distinct from one another, the plurality of conduits each comprising an internal reinforcement means, wherein the internal reinforcement means are configured to constrain lateral expansion of the plurality of actuation chambers as fluid is received thereto, wherein the radial stiffness of the internal reinforcement means is such that radial expansion of each of the plurality of actuation chambers is constrained, such that the effect of actuation of a first actuation chamber of the plurality of actuation chambers has on a second actuation chamber of the plurality of actuation chambers is limited.

2. A device according to claim 1, wherein the flexible body is enclosed in an external reinforcement means configured to constrain lateral expansion of the plurality of actuation chambers as fluid is received thereto, wherein the radial stiffness of the external reinforcement means is such that radial expansion of the plurality of actuation chambers is constrained.

3. A device according to claim 1, further comprising an outer sleeve encasing the plurality of segments configured in use to increase friction in either a first direction or both the first direction and a second opposing direction along the longitudinal axis of the device.

4. A device according to claim 3, wherein a surface of the outer sleeve comprises a plurality of fish scale or cilia-like projections moveable between a first position and a second position, wherein the first position comprises the plurality of fish scale or cilia-like projections being substantially parallel to the longitudinal axis of the device, and wherein the second position comprises the plurality of fish scale or cilia-like projections being substantially perpendicular to the longitudinal axis of the device.

5. A device according to claim 1, wherein the device is an endoscope.

* * * * *